(12) United States Patent
Tollini

(10) Patent No.: US 6,689,105 B2
(45) Date of Patent: Feb. 10, 2004

(54) SECURING TAPE ASSEMBLY

(76) Inventor: Dennis R. Tollini, 9193 Beech Meadow Ct., Clarence Center, NY (US) 14032

( * ) Notice: Subject to any disclaimer, the term of this patent is extended or adjusted under 35 U.S.C. 154(b) by 0 days.

(21) Appl. No.: 10/202,315

(22) Filed: Jul. 24, 2002

(65) Prior Publication Data

US 2002/0195114 A1 Dec. 26, 2002

Related U.S. Application Data

(63) Continuation of application No. 09/362,338, filed on Jul. 27, 1999, now Pat. No. 6,447,486.

(51) Int. Cl.[7] .................................................. A61M 5/32
(52) U.S. Cl. ........................ 604/180; 604/174; 604/178; 604/179
(58) Field of Search ................. 604/180, 179, 604/178, 177, 174; 128/DIG. 26

(56) References Cited

U.S. PATENT DOCUMENTS

| | | | |
|---|---|---|---|
| 3,288,136 A | 11/1966 | Lund | |
| 3,826,254 A | 7/1974 | Mellor | |
| 3,834,380 A | * 9/1974 | Boyd | .......................... 128/133 |
| 4,702,736 A | 10/1987 | Kalt et al. | |
| 4,838,878 A | 6/1989 | Kalt et al. | |
| 5,037,397 A | * 8/1991 | Kalt et al. | ................... 604/174 |
| 5,098,399 A | 3/1992 | Tollini | |
| 5,147,322 A | 9/1992 | Bowen et al. | |
| 5,266,401 A | 11/1993 | Tollini | |
| 5,300,037 A | * 4/1994 | Delk et al. | ................... 604/180 |
| 5,304,146 A | 4/1994 | Johnson et al. | |
| 5,520,656 A | 5/1996 | Byrd | |
| 5,575,802 A | 11/1996 | McQuilkin et al. | |
| 5,681,290 A | 10/1997 | Alexander | |

* cited by examiner

*Primary Examiner*—Long V. Le
*Assistant Examiner*—Ann Y Lam
(74) *Attorney, Agent, or Firm*—Joseph P. Gastel

(57) ABSTRACT

A securing tape assembly for securing a tube or a needle to a patient including an elongated tape having outer end portions for adhesive securement to the patient and a central portion which encircles a tube and a clip which is secured the central portion of the tape. The central portion may be a tab or an elongated portion between the end portions. The central portion may have foam material or blue adhesive on the side thereof which engages the tube. Also, the central portion may have hook fabric thereon which is placed into engagement with pile fabric on an end portion which is adhesively secured to the patient. The clip may have movable parts which are moved between open and closed positions or it may be a channel-shaped member.

15 Claims, 16 Drawing Sheets

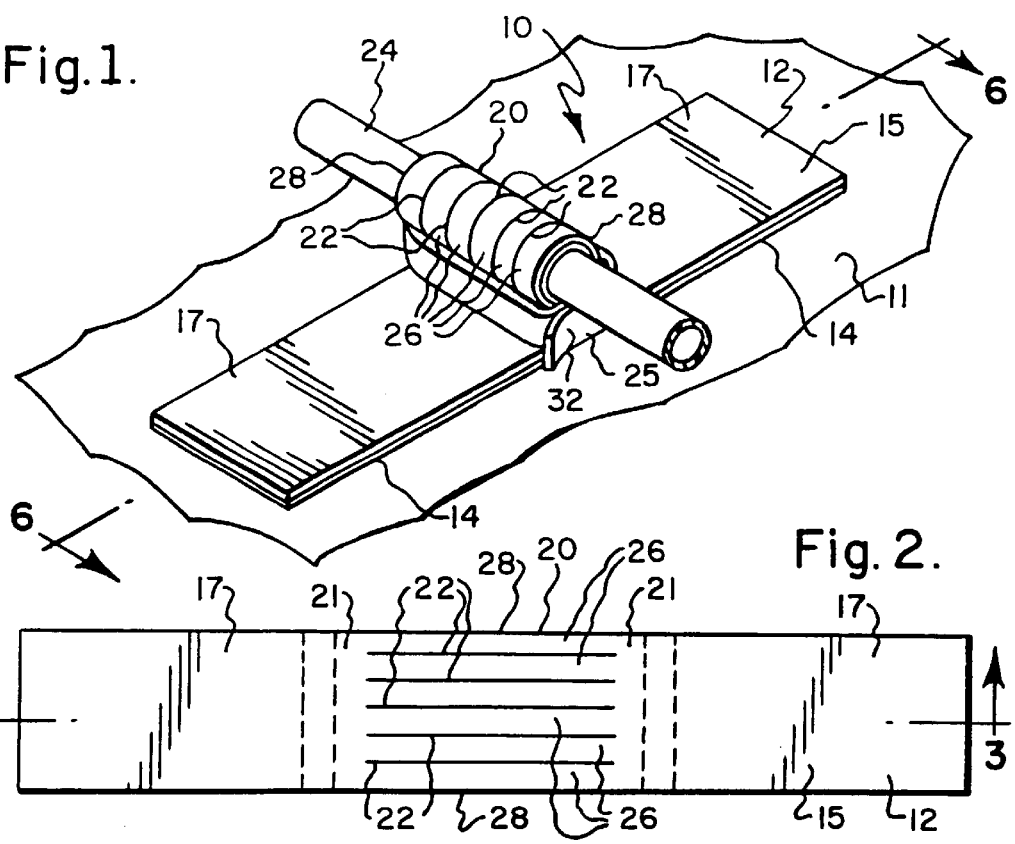

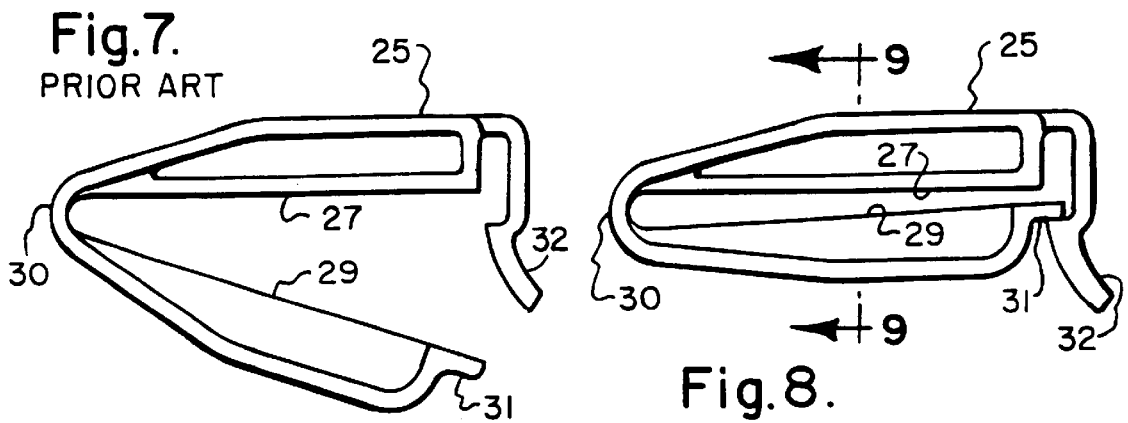
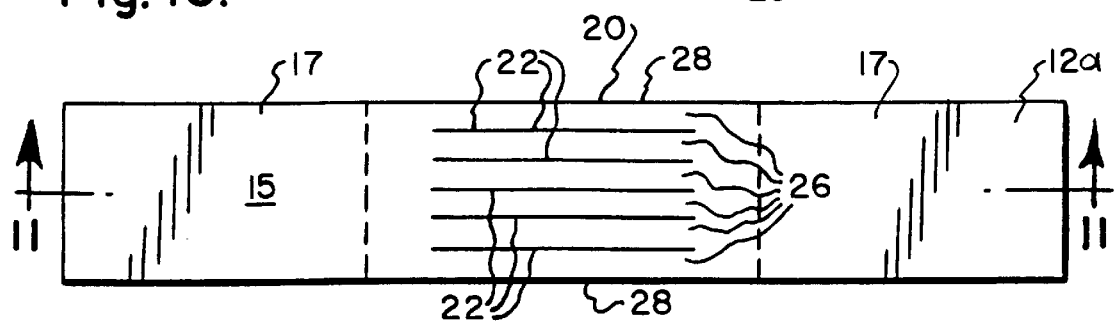
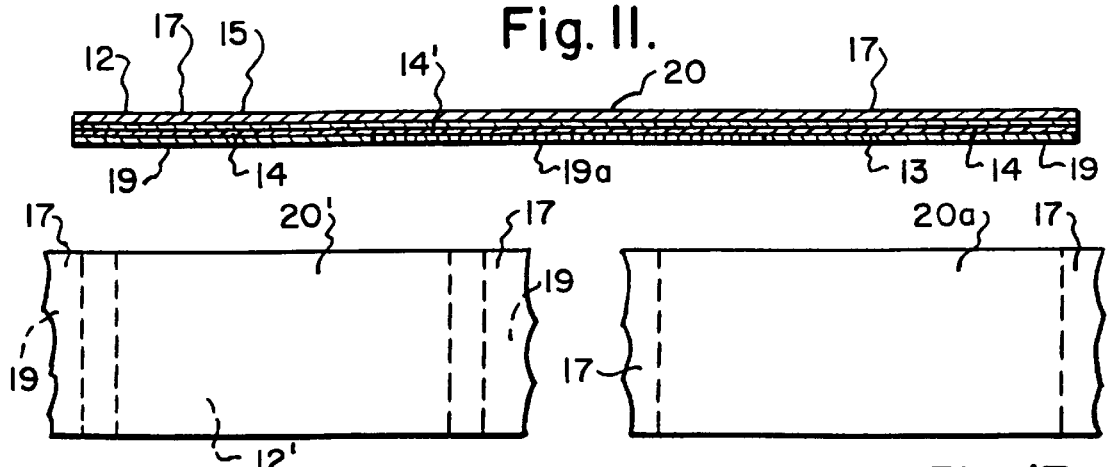
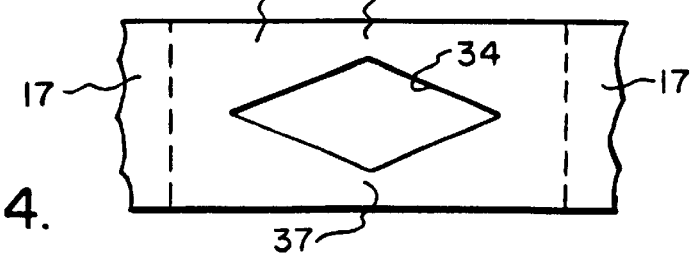

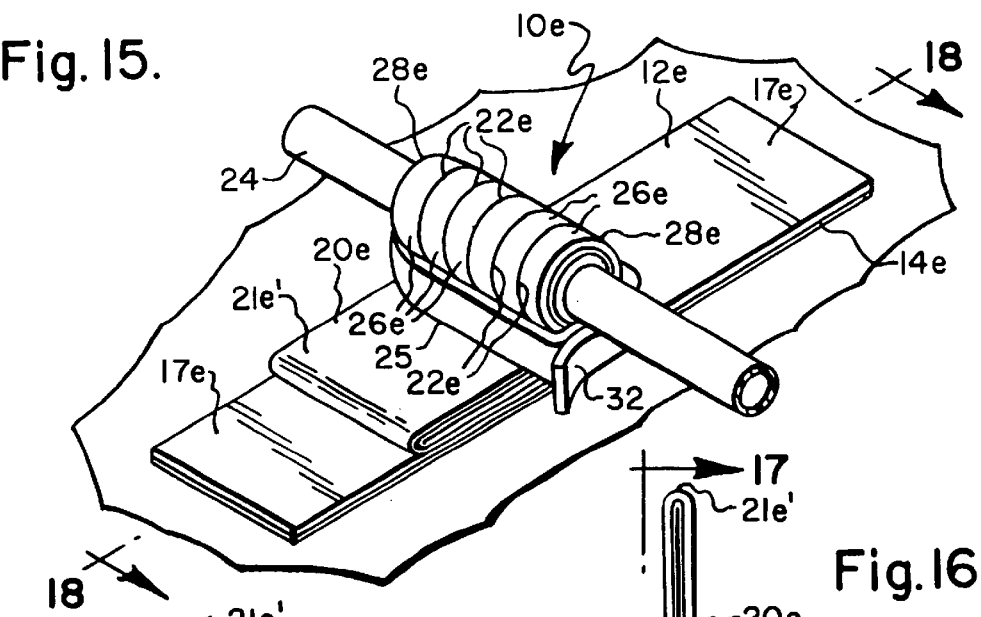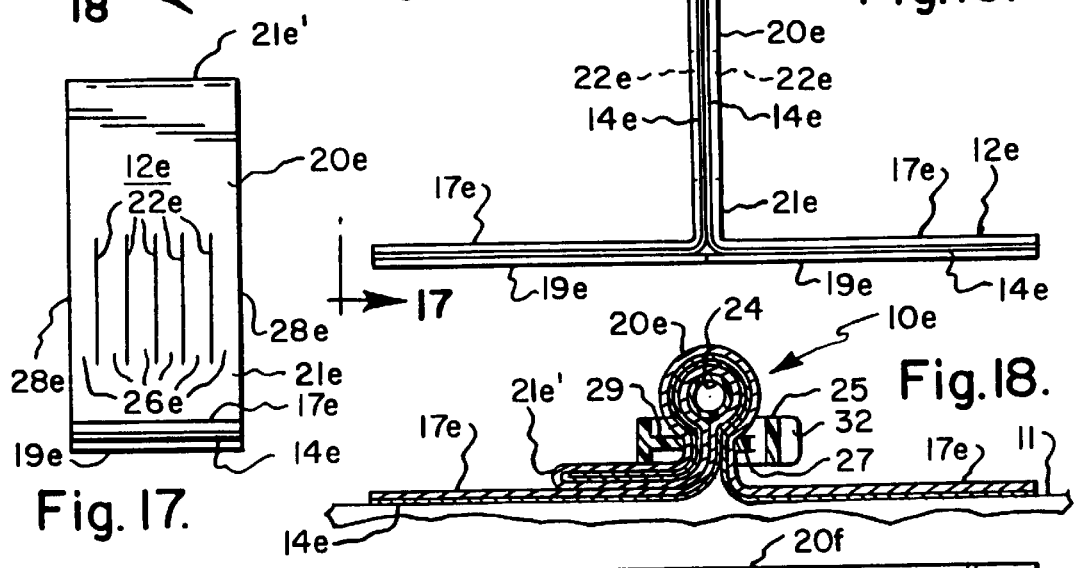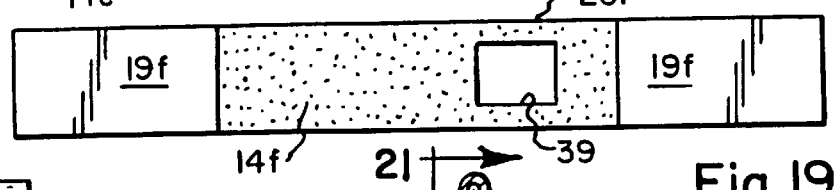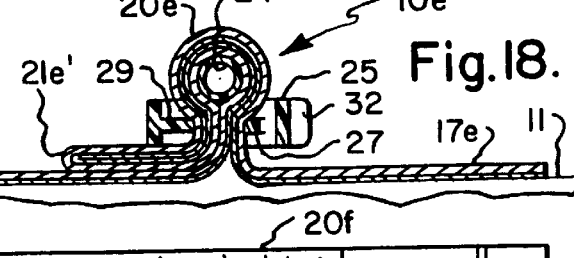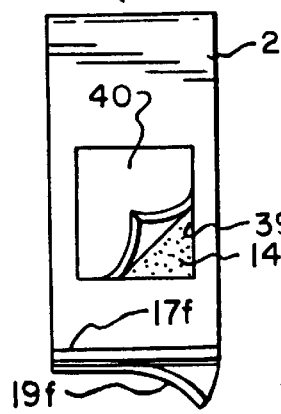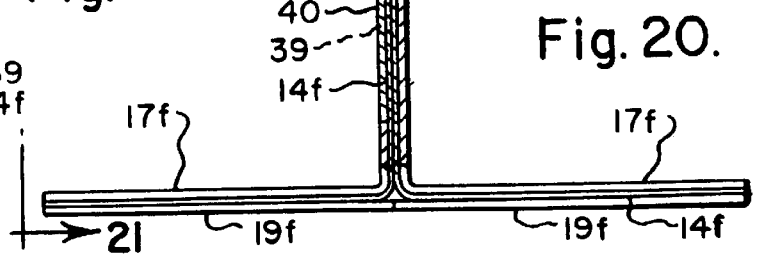

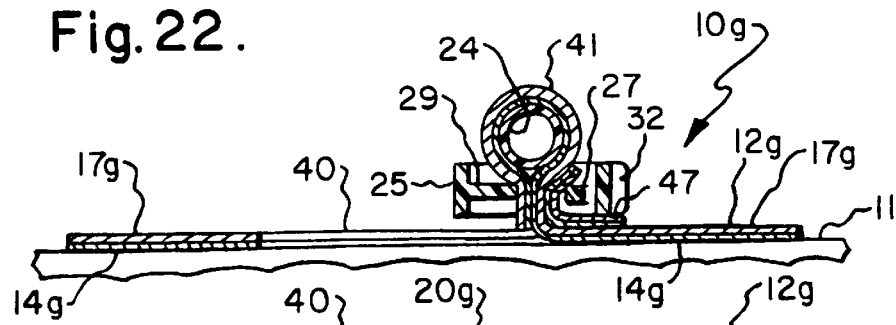
Fig. 22.
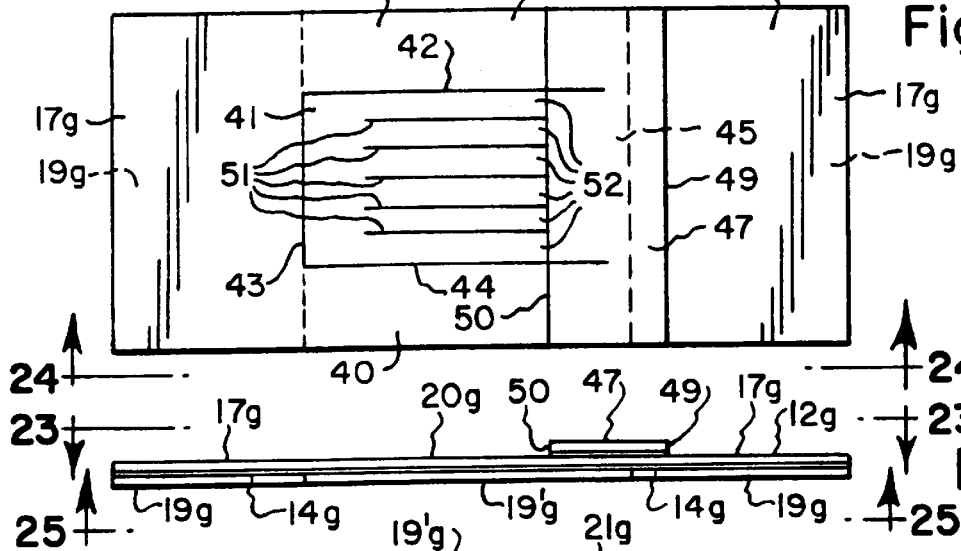
Fig. 23.
Fig. 24.
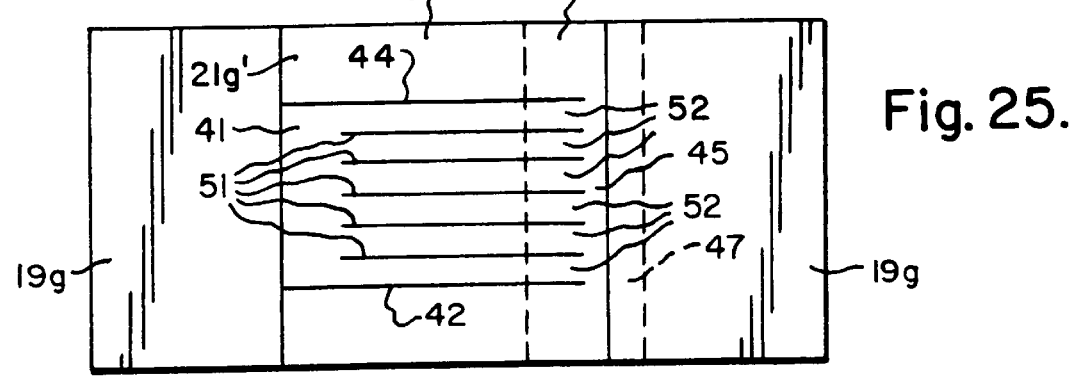
Fig. 25.
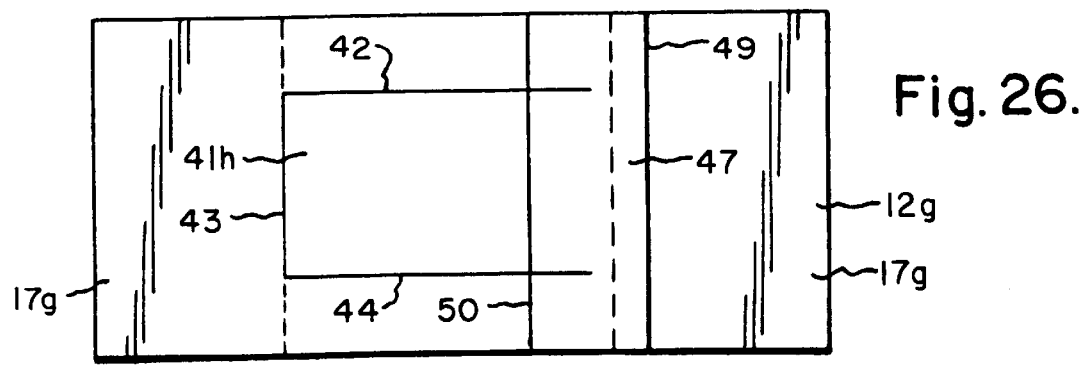
Fig. 26.

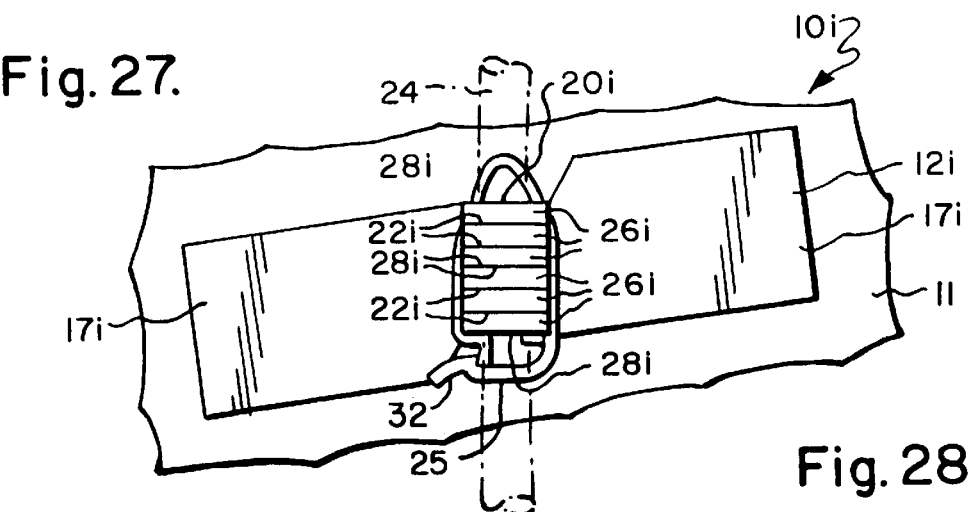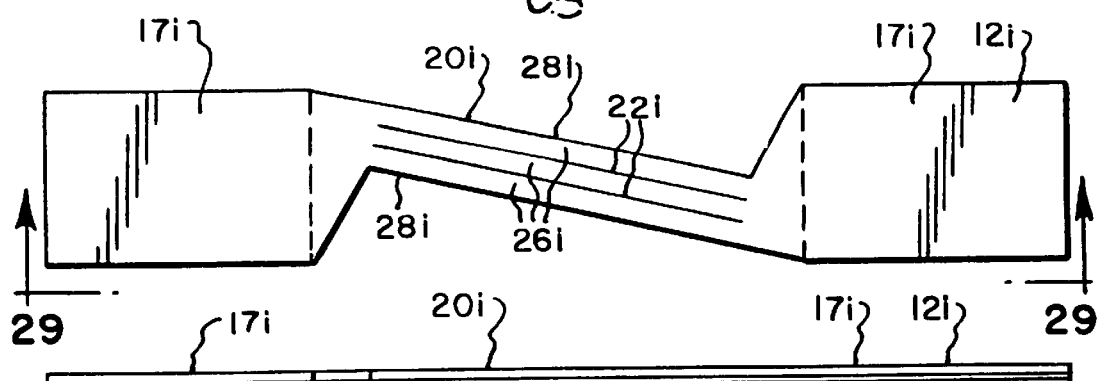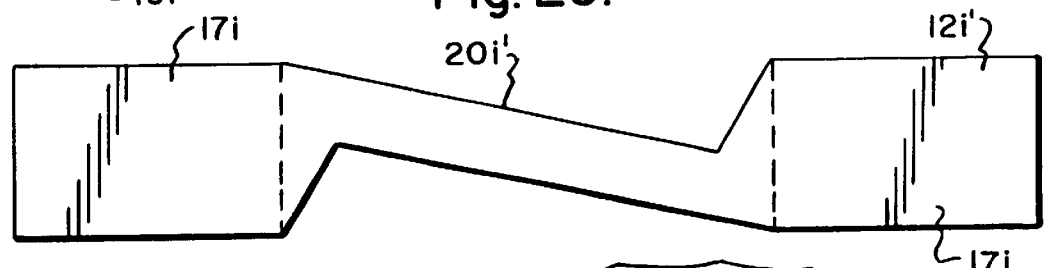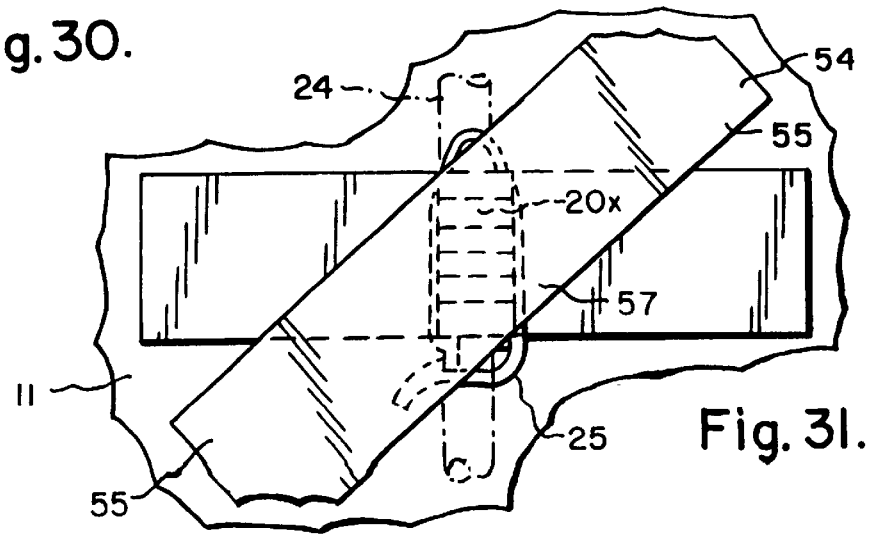

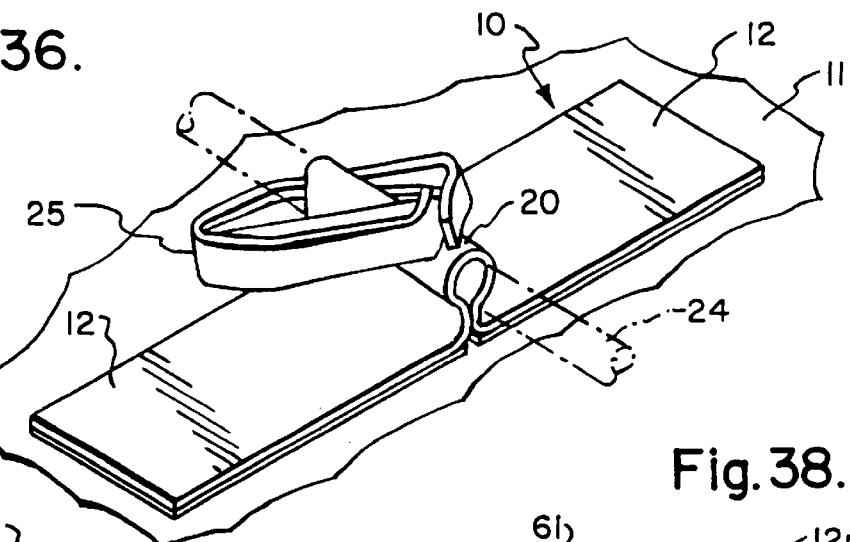
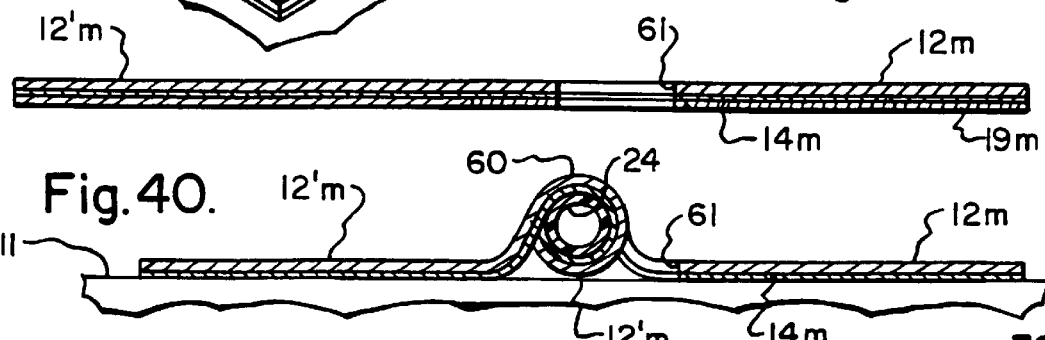
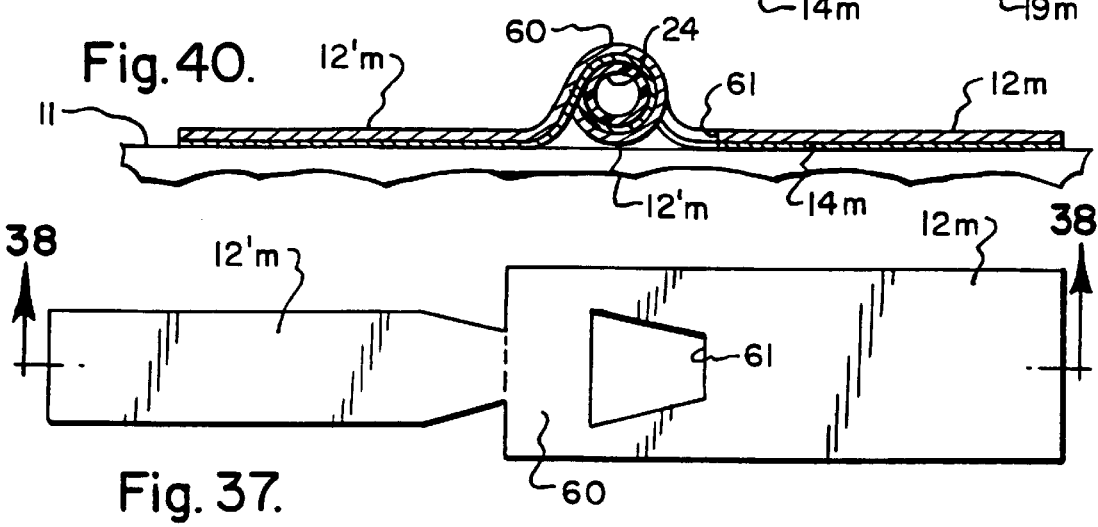
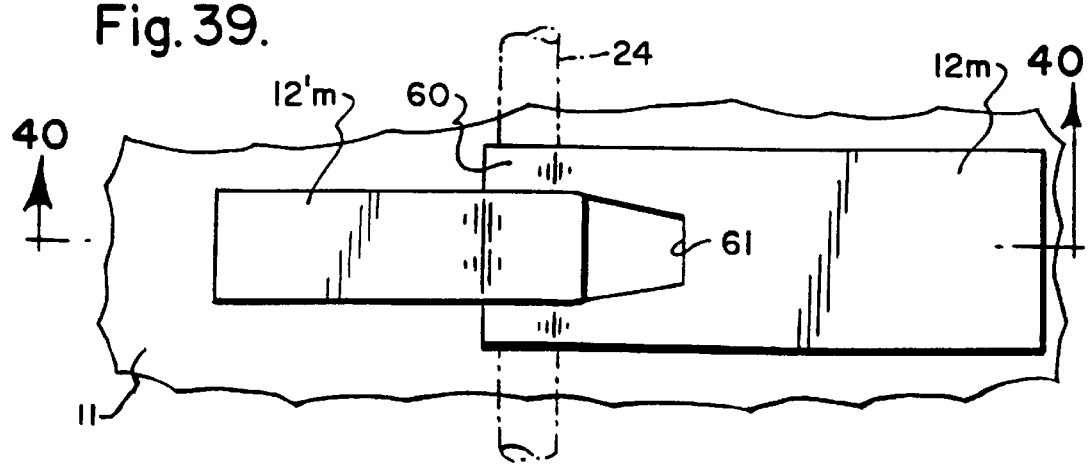

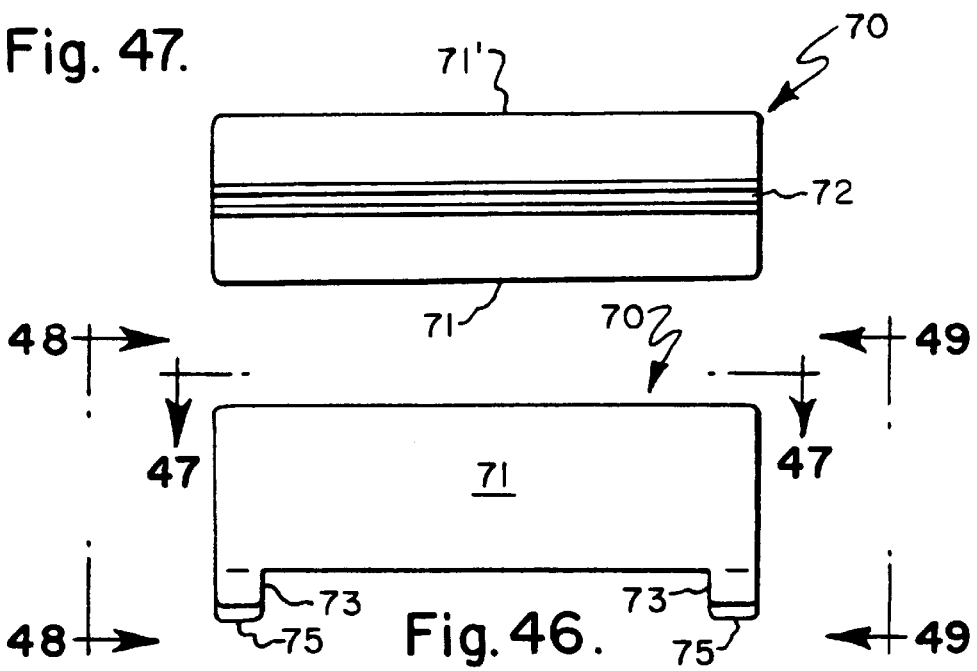
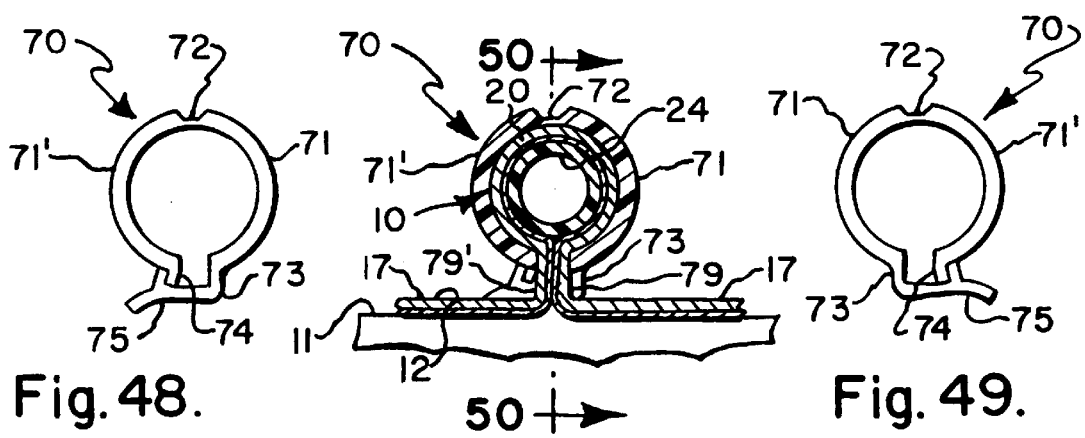
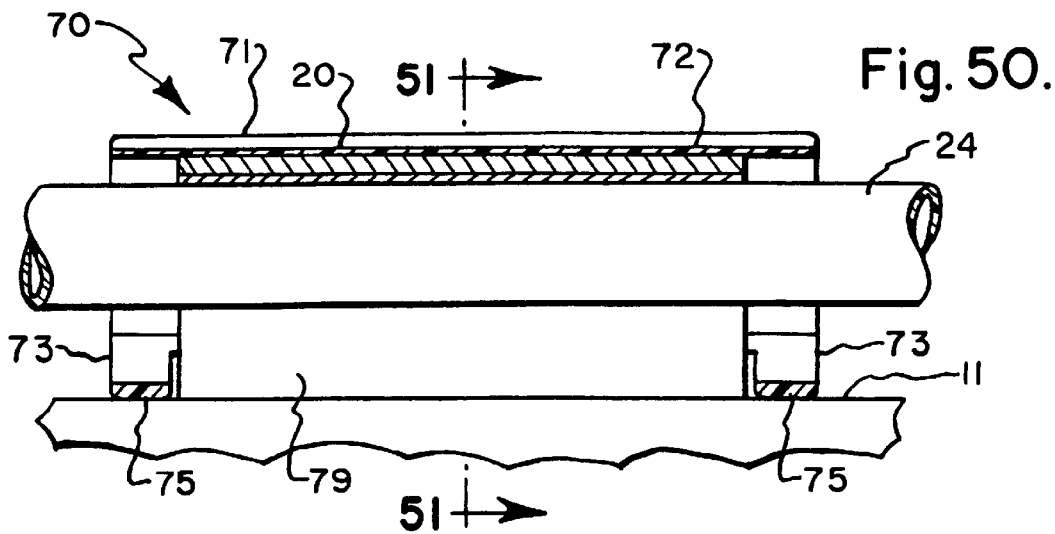

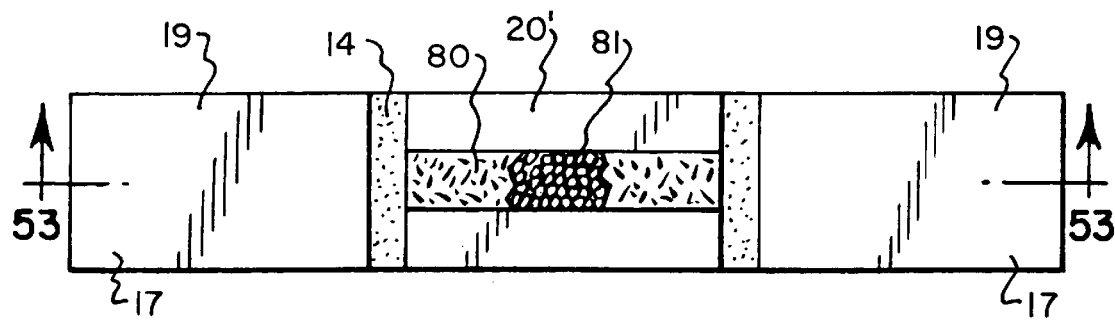
Fig. 52.
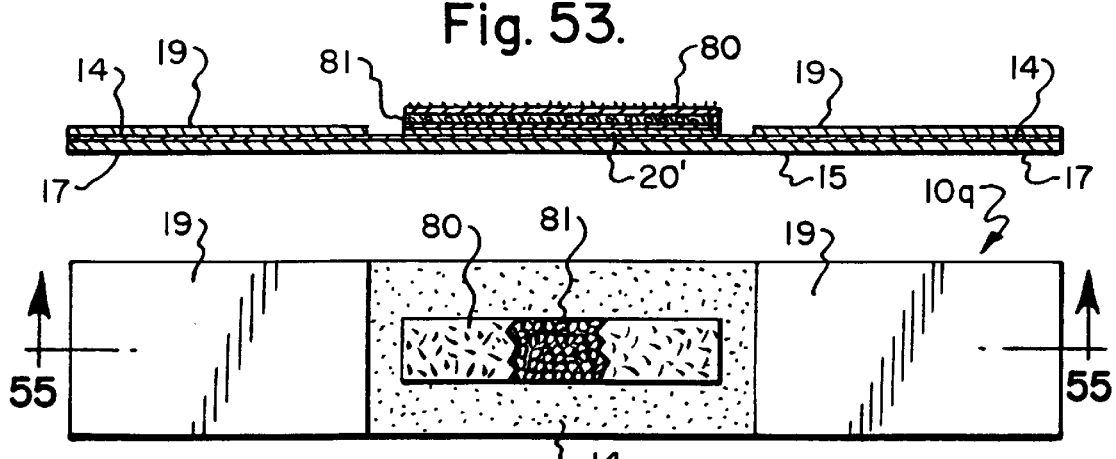
Fig. 53.
Fig. 54.
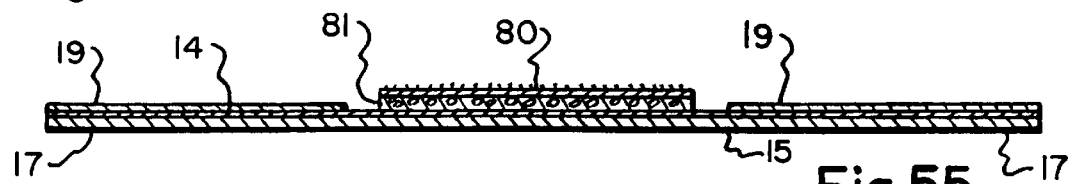
Fig. 55.
Fig. 56.
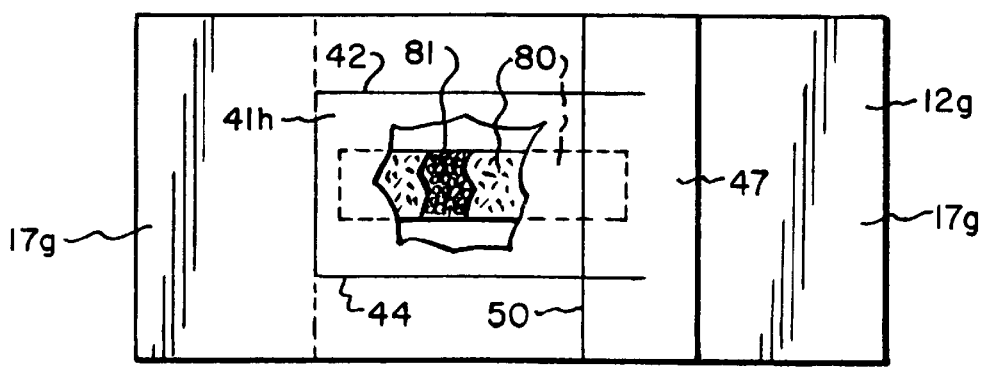

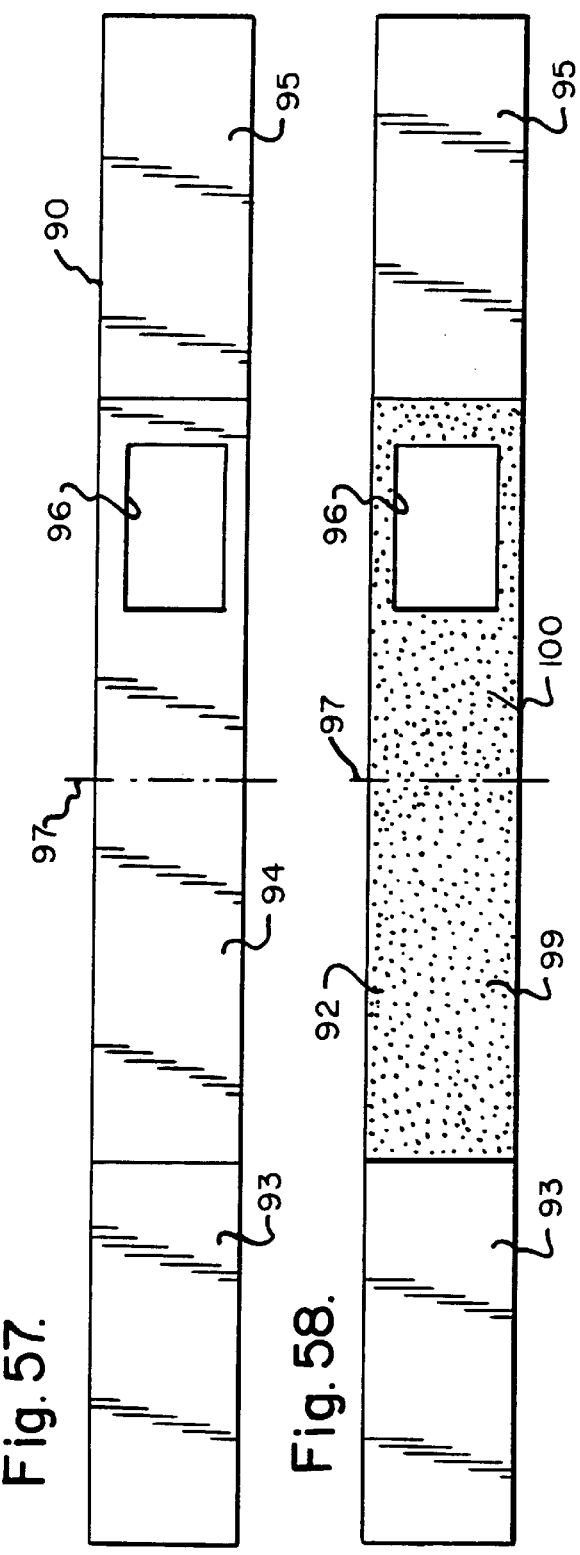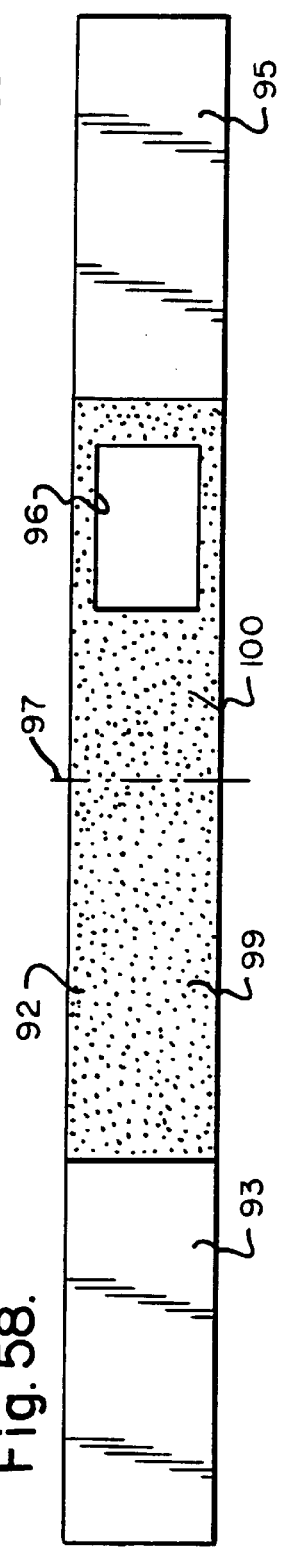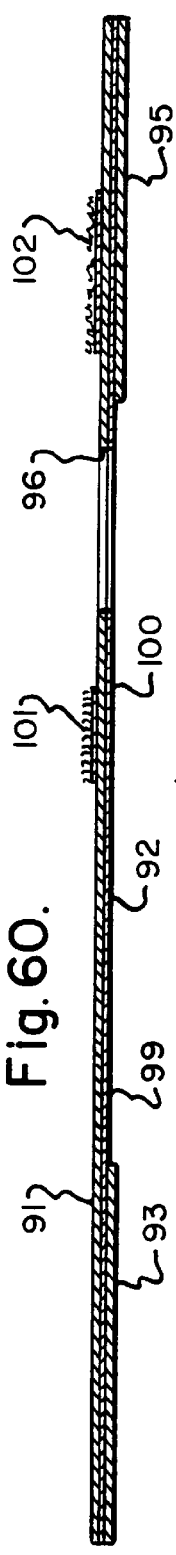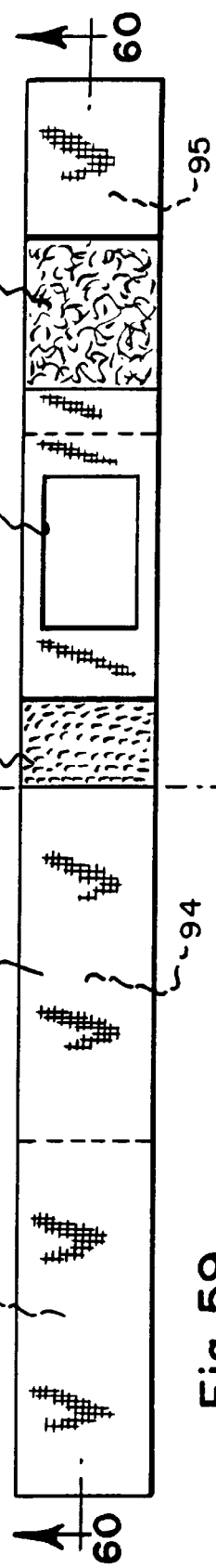

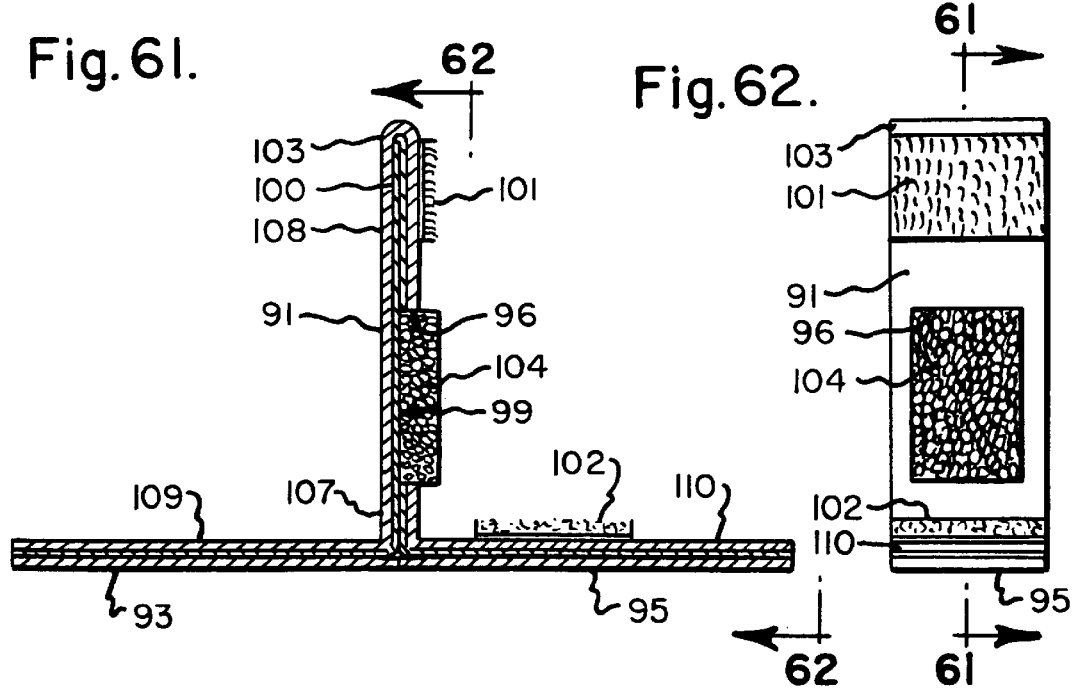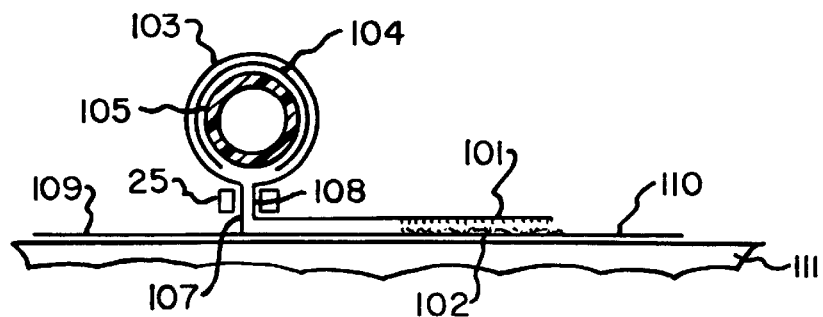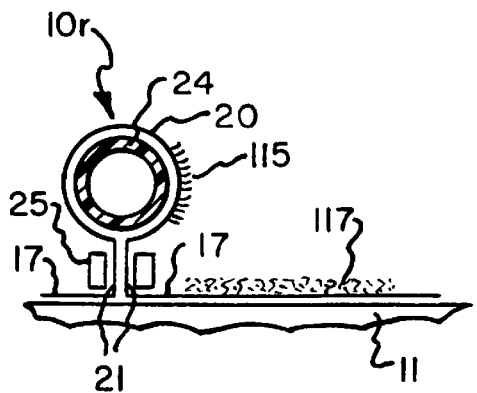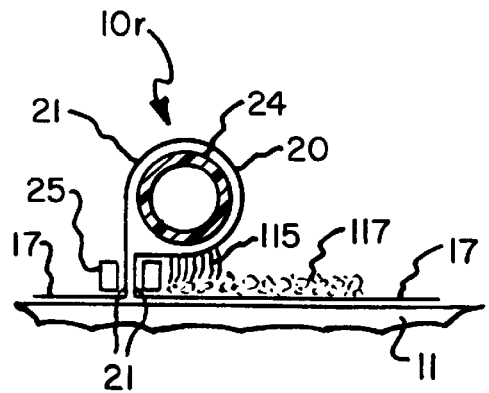

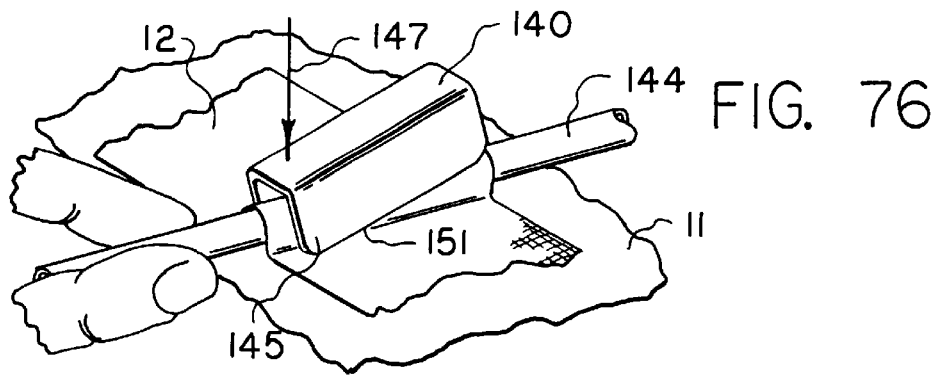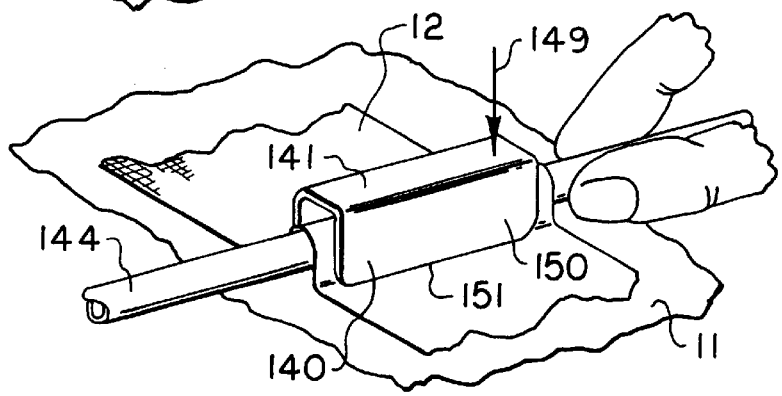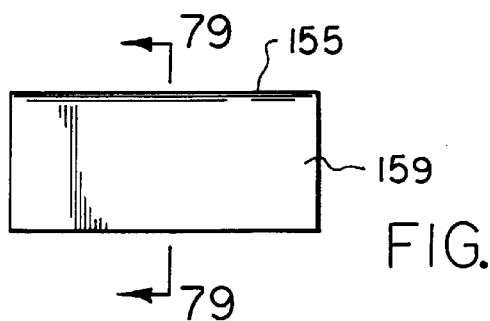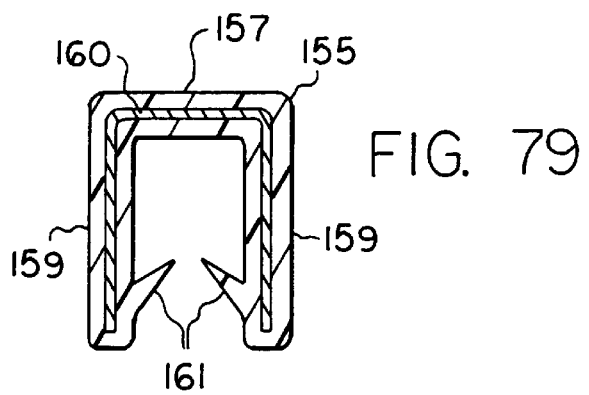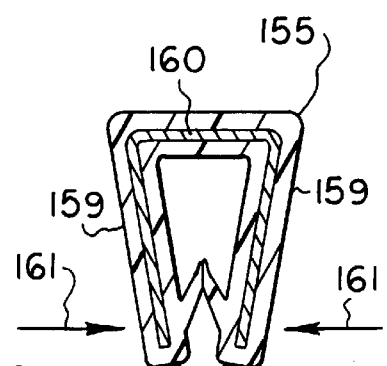

US 6,689,105 B2

SECURING TAPE ASSEMBLY

CROSS-REFERENCE TO RELATED APPLICATIONS

This application is continuation of U.S. application Ser. No., 09/362,338 filed on Jul. 27, 1999, now U.S. Pat. No. 6,447,486.

STATEMENT REGARDING FEDERALLY SPONSORED RESEARCH OR DEVELOPMENT

Not Applicable

BACKGROUND OF THE INVENTION

The present invention relates to an improved securing tape assembly for securing a tube to a patient's skin.

By way of background, silicone-type tubing is commonly used in medical applications for conducting fluids to and from a patient's body. In the past, insofar as known, it was difficult to positively secure such tubing in position with a securing tape because the adhesive of the securing tape would not positively adhere to the silicone tubing. In addition, the use of adhesive type of tape in certain circumstances was not desirable because the adhesive could attract unsanitary substances.

BRIEF SUMMARY OF THE INVENTION

It is accordingly one object of the present invention to provide securing tape assemblies having structure which will securely hold silicone tubing in position on a patient's skin.

Another object of the present invention is to provide an improved method of securing a tube relative to the skin of a patient.

A further object of the present invention is to provide a new combination of a tape, a tube and a clip for securing the tube to the tape.

Yet another object of the present invention is to provide an improved tape for securing a tube relative to the skin of a patient. Other objects and attendant advantages of the present invention will readily be perceived hereafter.

The present invention relates to a securing tape assembly comprising an elongated tape having an inner surface and an outer surface, outer end portions on said tape, a central portion on said tape between said outer end portions for engaging the central portion of a tube, and a clip for engaging the central portion at said outer surface of said tape for pressing said central portion against said tube.

The present invention also relates to a securing tape assembly comprising an elongated tape having an inner surface and an outer surface, first means on said tape for securing said tape to a patient, and second means for securing a tube relative to said first means.

The present invention also relates to the combination of a tube, a tape, and a clip securing said tube to said tape.

The present invention also relates to a method of securing a tube relative to the skin of a patient comprising the steps of securing a tape to said skin, engaging said tube with a portion of said tape, and applying a clip to said portion of said tape which engages said tube to firmly press said tape into engagement with said tube.

The present invention also relates to a securing tape comprising an elongated tape having an inner surface and an outer surface, outer end portions on said tape, adhesive on said inner surfaces of said outer end portions, a central portion on said tape between said outer end portions, and at least one longitudinal slit in said central portion.

The various aspects of the present invention will be more fully understood when the following portions of the specification are read in conjunction with the accompanying drawings wherein:

BRIEF DESCRIPTION OF THE SEVERAL VIEWS OF THE DRAWING

FIG. 1 is a fragmentary perspective view of one embodiment of a securing tape assembly of the present invention in position on a supporting surface such as a patient's skin and securing a tube in position relative thereto;

FIG. 2 is a plan view of the securing tape of the assembly in a flattened condition;

FIG. 3 is a cross sectional view taken substantially along line 3—3 of FIG. 2;

FIG. 4 is a cross sectional view similar to FIG. 3 with the release paper removed from the central portion of the tape;

FIG. 5 is a cross sectional view showing the configuration of the securing tape of the assembly relative to a tube before a clip is applied to the securing tape;

FIG. 6 is a cross sectional view taken substantially along line 6—6 of FIG. 1 and showing a tube clamped in the securing tape which is mounted on the skin;

FIG. 7 is a side elevational view of the prior art clip which is used in the embodiment of FIGS. 1–6 with the clip being in an opened condition;

FIG. 8 is a view similar to FIG. 7 but showing the prior art clip in a closed position;

FIG. 9 is a cross sectional view taken substantially along line 9—9 of FIG. 8;

FIG. 10 is a plan view of another embodiment of a securing tape;

FIG. 11 is a cross sectional view taken substantially along line 11—11 of FIG. 10;

FIG. 12 is a fragmentary plan view of another securing tape embodiment of the present invention;

FIG. 13 is a fragmentary plan view of still another securing tape embodiment of the present invention;

FIG. 14 is a fragmentary plan view of yet another securing tape embodiment of the present invention;

FIG. 15 is a fragmentary perspective view of another securing tape embodiment of the present invention;

FIG. 16 is a side elevational view of the securing tape of FIG. 15 showing the structure thereof before it was placed in the condition of FIG. 15;

FIG. 17 is a side elevational view taken substantially in the direction of arrow 17—17 of FIG. 16;

FIG. 18 is a fragmentary cross sectional view taken substantially along line 18—18 of FIG. 15;

FIG. 19 is a plan view of a blank which is used for yet another securing tape embodiment of the present invention;

FIG. 20 is an enlarged side elevational view partially in cross section of the blank of FIG. 19 after it has been formed into a securing tape for use;

FIG. 21 is an end elevational view taken substantially in the direction of arrows 21—21 of FIG. 20;

FIG. 22 is a cross sectional view of yet another embodiment of a securing tape assembly showing a tube held in position when the securing tape is mounted on a surface;

FIG. 23 is a plan view taken substantially in the direction of arrows 23—23 of FIG. 24 of the securing tape of FIG. 22 before it has been placed in the condition shown in FIG. 22;

FIG. 24 is a side elevational view taken substantially in the direction of arrows 24—24 of FIG. 23;

FIG. 25 is a bottom plan view taken substantially in the direction of arrows 25—25 of FIG. 24;

FIG. 26 is a plan view similar to FIG. 23 but showing another embodiment of a securing tape;

FIG. 27 is a fragmentary plan view of yet another embodiment of a securing tape assembly mounted on a foreign body;

FIG. 28 is a plan view of the securing tape of FIG. 27 in flattened form;

FIG. 29 is a side elevational view of the securing tape taken substantially in the direction of arrows 29—29 of FIG. 28;

FIG. 30 is a plan view similar to FIG. 28 but showing yet another embodiment of the securing tape of the present invention;

FIG. 31 is a plan view of a securing tape assembly such as shown in FIG. 1 and having a cross tape mounted thereon for the purpose of covering the raised portions which are obtained when a tube is being held in position by the securing tape assembly;

FIG. 36 is a fragmentary perspective view of a modified manner in which a securing tape assembly of the present invention may be utilized in practice;

FIG. 37 is a plan view of yet another securing tape embodiment of the present invention which does not utilize a clip;

FIG. 38 is a cross sectional view taken substantially along line 38—38 of FIG. 37;

FIG. 39 is a plan view showing the embodiment of FIG. 37 securing a tube to the skin of a patient;

FIG. 40 is a cross sectional view taken substantially along line 40—40 of FIG. 39;

FIG. 46 is a side elevational view of another type of clip which can be used with tapes of the present invention which have clips associated therewith;

FIG. 47 is a plan view of the clip of FIG. 46 taken substantially in the direction of arrows 47—47 of FIG. 46;

FIG. 48 is an end elevational view taken substantially in the direction of arrows 48—48 of FIG. 46;

FIG. 49 is a end elevational view taken substantially in the direction of arrows 49—49 of FIG. 46;

FIG. 50 is an enlarged fragmentary view showing the clip of FIG. 46 in position on a securing tape;

FIG. 51 is a fragmentary cross sectional view taken substantially in the direction of arrows 51—51 of FIG. 50;

FIG. 52 is a plan view of another securing tape embodiment of the present invention which is used with a clip;

FIG. 53 is a cross sectional view taken substantially along line 53—53 of FIG. 52;

FIG. 54 is a plan view of still another securing tape embodiment of the present invention which is used with a clip;

FIG. 55 is a cross sectional view taken substantially along line 55—55 of FIG. 54;

FIG. 56 is a plan view of still another securing tape embodiment of the present invention which is used with a clip;

FIG. 57 is a plan view of the underside of a blank having release paper thereon for another securing tape embodiment of the present invention which is used with a clip;

FIG. 58 is a view similar to view 57 but showing the release paper removed from a central portion thereof;

FIG. 59 is a plan view of the top side of the blank with hook and pile fabric applied thereto;

FIG. 60 is a cross sectional view taken substantially along line 60—60 of FIG. 59;

FIG. 61 is a cross sectional view taken substantially along line 61—61 of FIG. 62 and showing foam material adhered to a tab which has been formed on the securing tape;

FIG. 62 is an end elevational view taken substantially in the direction of arrows 62—62 of FIG. 61;

FIG. 63 is a schematic view of a securing tape assembly with the tape portion of FIGS. 57–62 mounted on the skin of a patient;

FIG. 64 is a schematic fragmentary side elevational view of another securing tape assembly embodiment of the present invention formed about a tube prior to being mounted in its final position on the skin of a patient;

FIG. 65 is a view similar to FIG. 64 showing the securing tape mounted in its final position on the skin of a patient;

FIG. 76 is a fragmentary perspective view illustrating the manner of mounting the clip of FIGS. 73–75 onto a securing tape mounted on the skin of the patient;

FIG. 77 is a fragmentary perspective view similar to FIG. 76 showing the final step of mounting the clip on the securing tape;

FIG. 78 is a side elevational view of yet another clip of the same general type of that shown in FIGS. 73–77;

FIG. 79 is a cross sectional view taken along line 79—79 of FIG. 78; and

FIG. 80 is a cross sectional view similar to FIG. 79 but showing how the clip of FIGS. 78 and 79 is manipulated after it has been placed in position about a securing tape.

DETAILED DESCRIPTION OF THE INVENTION

Figure 32:
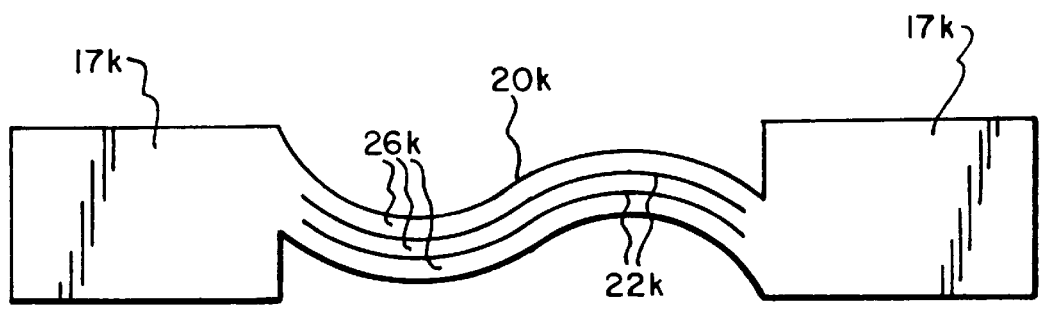
FIG. 32 is a plan view of yet another securing tape embodiment of the present invention.

Summarizing briefly in advance, the improved securing tape embodiments of the present invention, including those which do and do not include a clip, are for the purpose of securely holding tubular members, primarily those of silicone rubber, against movement relative to the portion of a patient's body to which they have been attached.

One embodiment of the present invention is disclosed in FIGS. 1–9. The securing tape assembly 10 is shown adhesively secured to the skin surface 11 of a patient. The securing tape assembly consists of an elongated tape 12 having an inner surface 13 with pressure-sensitive adhesive 14 thereon and a nonadhesive outer surface 15. The securing tape 12 has outer end portions 17, which, in use, are adhesively secured to the skin surface 11 of the patient. In order to so secure end portion 17, release paper 19 is first removed from the surface of the adhesive. A central portion 20 is located between the two outer end portions 17, and central portion 20 has end portions 21 which are adjacent end portions 17. Central portion 20 has a plurality of slits 22 therein which extend longitudinally of central portion 20. The inner surface of the securing tape at pressure-sensitive adhesive 14 has a piece of tape 12' secured thereto by the adhesive 14' in adhesive-to-adhesive relationship. The tape 12' is the same material as described above relative to tape 12. The slits 22 extend through both tape 12 and tape 12'. Release paper 19' covers tape 12' and extends beyond it so that the ends 23 of release paper 19' are adhesively secured to adhesive layer 14.

In use, and prior to the application of the securing tape assembly 10 to the position shown in FIG. 1, the release paper 19' is removed from the position of FIG. 3 so as to expose the nonadhesive surface of the tape portion 12', as shown in FIG. 4. Thereafter, the central portion 20 is conformed to a portion of the outer periphery of tube 24, as shown in FIG. 5, and thereafter a clip 25 is pressed against the outer surface of securing tape 12 at end portions 21 of central portion 20 to thereby securely clip the central portion 20 of the securing tape about the outer periphery of tube 24, as shown in FIGS. 1 and 6. Thereafter, the release paper 19 is removed from adhesive layers 14 to provide the assembly shown in FIG. 6, and thereafter the outer end portions 17 are adhesively secured to the skin surface 11 of the patient's body.

The clip 25 is a prior art device fabricated of plastic and its normal unclamped position is as shown in FIG. 7 wherein sides 27 and 29 are biased to an open position about pivot portion 30. In use, the sides 27 and 29 are clamped about the end portions 21 of the securing tape, as described above, and the projection 31 is engaged by latch 32 to maintain the clip in the closed position shown in FIGS. 1, 6 and 8. It will be appreciated that the clip of FIGS. 7–9 is shown only by way of example and not of limitation inasmuch as any type of clip which holds the central end portions 21 together can be used, provided that the clip can be released to remove the securing tape 10 from the tube 24. In the present instance, clip 25 is removed by merely swinging latch 32 away from projection 31, and the spring provided at pivot 30 will automatically cause the clip 25 to return to its position of FIG. 7.

It is to be especially noted that the slits 22 of securing tape 10 permit the bands 26 to each individually conform to the tube 24. Furthermore, the edges of at least some of the bands 26, as defined by slits 22 and outer edges 28, can conform onto tube 24 if the strips 26 are not perfectly flat on tube 24.

In FIGS. 10 and 11 another embodiment of a securing tape 12a is shown. In this embodiment all features which are common to the embodiment of FIGS. 1–9 bear identical numerals and therefore the description thereof will be omitted at this juncture. The embodiment of FIG. 10 does not have the liner 12' of FIGS. 3 and 4. Only a piece of release paper 19a, which is analogous to release paper 19' of FIG. 3, covers the adhesive 14' on the central portion 20 of the securing tape. In certain instances it may be desirable to take advantage of the adhesive 14' by causing it to adhere to a tube. However, in most instances it is desirable to use the embodiment shown in FIGS. 3 and 4 with the tape 12' on the central portion because in certain instances foreign objects can undesirably adhere to the central portion of the tape.

In FIG. 12 another securing tape embodiment is shown in plan. This embodiment is identical in all respects to the embodiment of FIGS. 1–9 except that the central portion 20', which is analogous to the central portion 20 of FIGS. 3 and 4, does not have any slits therein.

In FIG. 13 another securing tape embodiment is shown which is identical in all respects to the embodiment of FIGS. 10 and 11 except that the central portion 20a, which is analogous to the central portion 20 of FIG. 10, does not have any slits therein.

In FIG. 14 yet another securing tape embodiment is shown which may be identical in all respects to any of the embodiments of FIGS. 1–11 except that the central portion 20d, which is analogous to the central portion 20 of any of FIGS. 1–10, has a diamond-shaped cutout 34 therein, so that in essence there are two separate bands 35 and 37 on opposite sides of the diamond. In fact the cutout can be rectangular with its long side extending lengthwise of the tape, or there can be a plurality of cutouts in the central portion 20d such that the central portion 20d in essence has a plurality of separated longitudinally extending bands.

Another securing tape assembly 10e is shown in FIGS. 15–18 and the associated securing tape is shown in FIGS. 16 and 17. The securing tape 12e is fabricated from a single piece of tape having a nonadhesive outer surface and a pressure-sensitive adhesive inner surface 14e. The securing tape 12e also has a central portion 20e which is formed by causing the adhesive inner surface 14e to adhere to itself, thereby producing the central portion 20e in tab form. The tab 20e has an end portion 21e secured to the end portions of tape end portions 17e, and it also has another end portion 21e' which is unattached. Thus, there are two end portions 17e which can adhere to a patient's skin 11 after the release paper 19e is removed. The central portion 20e has a plurality of slits 22e therein which define bands 26e in conjunction with outer edges 28e of tab 20e. The method of fabricating a securing tape having an integral upstanding tab such as 20e is further described relative to FIGS. 57–62.

In use, securing tape 12e has its outer end portions 17e secured to the patient 11 and thereafter the tab 20e is wound around the tube 24 and thereafter the clip 25 is secured as shown to firmly clip the tube 24 in position.

In FIGS. 19–21 another securing tape embodiment is shown. This embodiment may be identical in all respects to the embodiment of FIGS. 16 and 17 except that the central portion tab 20f is fabricated so that there is a cutout 39 in one side of tab 20f. This cutout is fabricated by removing a piece 40 from one side of tab 20f leaving exposed the adhesive 14f which covers one side of the tape. The securing tape thus has an adhesive surface 14f on its two end portions 17f which are secured to the patient 11, and the adhesive 14f on end portion 17f are covered by release paper 19f which is removed, as is well known. The advantage of the embodiment of FIGS. 19–21 is that there is exposed adhesive 14f in window 39 of tab 20f, as this adhesive may be desirable for adhering the tab 20f to the tube 24 under certain circumstances. The embodiment of FIGS. 19–21 is used in a securing tape assembly with a clip 25 in the manner shown in FIG. 18.

Another securing tape assembly 10g is shown in FIGS. 22–25. The securing tape 12g is fabricated from a piece of tape having a nonadhesive outer surface and a pressure-sensitive adhesive inner surface 14g which is covered by three pieces of release paper 19g which cover the adhesive on end portions 17g, and release paper 19'g which cover the adhesive on central portion 20g. Central portion 20g includes two outer side portions 40 which adhere to the patient 11 and a central tab 41 which has sides 42, 43 and 44 and is hinged to one of the end portions 17g at 45. A reinforcing strip 47 having borders 49 and 50 is adhesively secured to outer surface 12g as shown. Tab 41 has a plurality of slits 51 therein which thus define separate bands 52. The outer bands 52 are also defined by outer edges 42 and 44.

In use, the release paper 19g is removed from ends 17g and from central portion 20g, and the ends 17g and the portions 40 of the securing tape are adhered to the patient 11. The tab 41 is extended and wrapped around tube 24 as shown in FIG. 22 and thereafter a clip 25 is secured to the outer end portions 21g and 21g' of tab 41 to firmly clip tube 24 in position. While FIGS. 22–25 have shown the adhesive surface 14g of the tab 41 engaging tube 24, it will be appreciated that, if desired, a piece of tape can be secured to the inside surface of tab 41, in the manner discussed above relative to FIGS. 1–6 so that there will be no adhesive engagement between tab 41 and tube 24.

Another securing tape embodiment is shown in FIG. 26. This embodiment is identical in all respects to the tape of FIGS. 23–25, as described above, except that the tab 41h does not have any slits therein.

In FIGS. 27 a further securing tape assembly 10i is shown and in FIGS. 28 and 29 a securing tape 12i is shown which is used in the assembly 10i of FIG. 27. Tape 12i has a nonadhesive outer surface and a pressure-sensitive adhesive inner surface 14i. Tape 12i also has end portions 17i and a central portion 20i which has slits 22i and outer edges 28i, all of which define bands 26i. The central portion 20i extends obliquely to end portions 17i. The end portions 17i are covered by release paper 19i and the central portion 20i is covered by release paper 19'i.

In use the release paper 19i is removed from the ends and one end 17i is adhered to the skin 11. Thereafter, the release paper 19'i is removed from the central portion 20i and the central portion is wrapped twice about tube 24. After the central portion 20i has been wound around tube 24, a clip 25 is secured as shown at the end portions of central portion 20i in the manner described above relative to the preceding figures. Thereafter, the release paper is removed from the other end portion 17i which is then adhered to the skin 11 of the patient. If desired, the central portion 20i may have a piece of tape secured to the adhesive underside as described above relative to FIGS. 3 and 4 so that there will be non-adhesive securement between the central portion 20i and the tube 24.

In FIG. 30 another securing tape embodiment 12i' is shown which is identical in all respects to the tape embodiment 12i of FIGS. 28–29 except that the central portion 20i' does not have the slits 22i therein.

Relative to the tapes such as shown in FIGS. 28–30, it will be appreciated, if desired, they can be applied in the above-described manner except that the clip 25 can be omitted because after one end portion 17i is secured to the patient's skin, the central portion 20i or portion 20'i can be wound tightly around the tube 24 and thereafter the other end portion 17i can be adhesively secured to the patient's skin.

In FIG. 31, there is a representation of a plain piece of adhesive tape 54 having a nonadhesive outer surface and a pressure-sensitive adhesive inner surface wherein the end portions 55 are adhesively secured to the patient 11 and the central portion 57 is placed in overlying relationship to the protruding central portion 20x which is representative of the central portion of any of the preceding embodiments of the securing tapes. The overlying tape 54 thus covers the protrusion at 20x so that it cannot snag on foreign objects.

Figure 33:
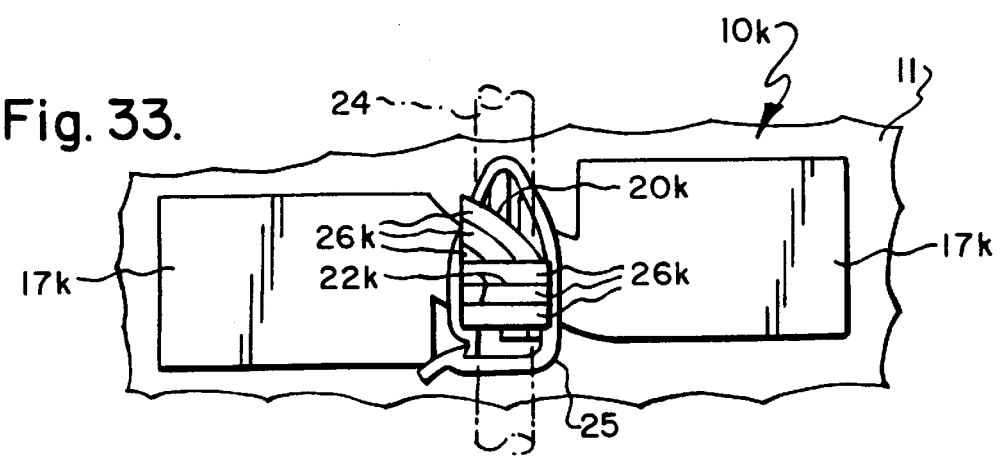
FIG. 33 is a plan view of a securing tape assembly including the securing tape embodiment of FIG. 32 mounted on the skin of a patient.

In FIG. 33 another securing tape assembly 10k is shown, and the tape used in this embodiment is also shown in FIG. 32. The tape of this embodiment is identical in all respects to the tape of FIGS. 28 and 29 except that the central portion 20k is curved as shown and it has a plurality of bands 26k which are separated by slits 22k. In use the central portion 20k is wound around a tube 24 as shown and the ends 17k are adhesively attached to the patient's skin 11. The curvature in the central portion 20k causes an overlapping of the bands 26k as shown in FIG. 33. Thus, the entire width of the overlapped bands is less than the width shown in FIG. 27 wherein all of the bands are side-by-side. The underside of the bands 26k may have exposed adhesive or a liner may be adhesively secured to the bands in case adhesive contact with tube 24 is not desired. The tape of this embodiment may be used without a clip, as discussed relative to the embodiment of FIGS. 28–30.

Figure 34:
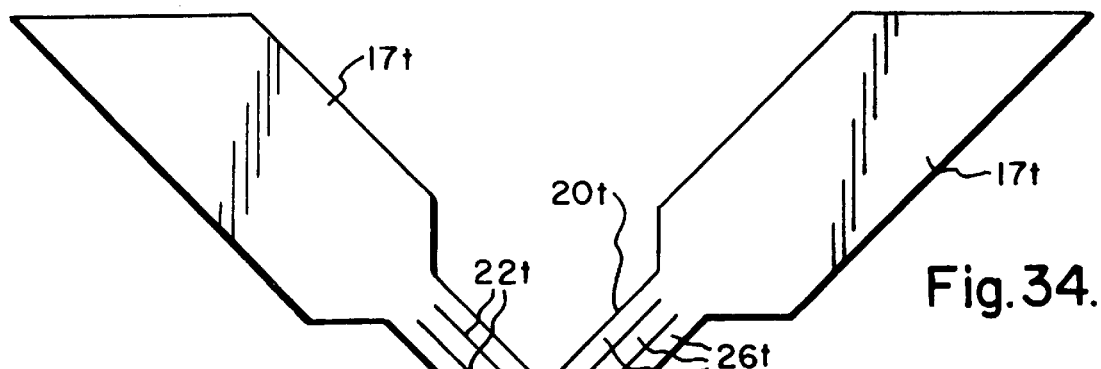
FIG. 34 is a plan view of yet another securing tape embodiment of the present invention.
Figure 35:
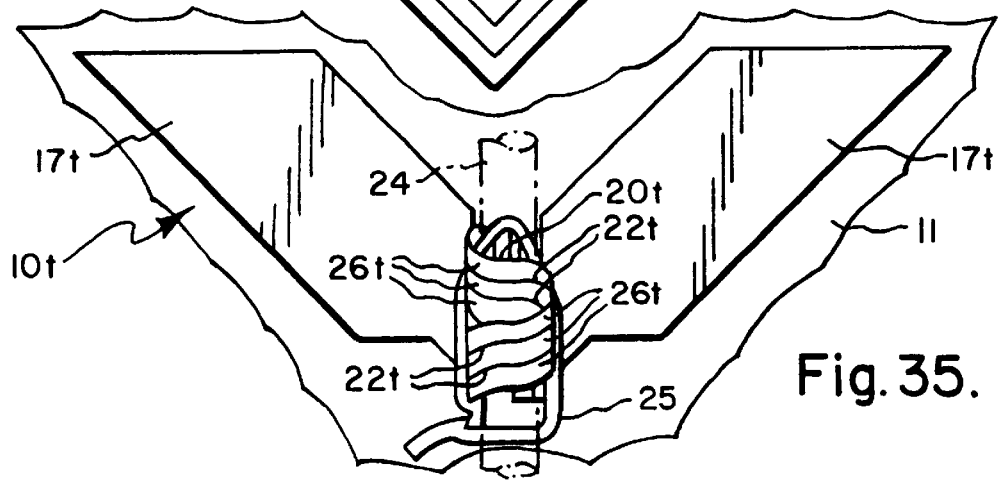
FIG. 35 is a plan view of a securing tape assembly including the securing tape embodiment of FIG. 34 mounted on the skin of a patient.

In FIG. 35 a further securing tape assembly 10t is shown and the tape used therein is also shown in FIG. 34. The tape has end portions 17t and a central portion 20t in the form of a Chevron. In use the central portion 20t is wound around the tube 24 and the ends 17t are adhesively secured to the skin 11. The central portion 20t has bands 26t which are separated by slits 22t. The undersurface of bands 26t may have exposed pressure-sensitive adhesive or the adhesive may be covered with a liner as expressed above relative to FIG. 5. The non-straight central portions of the embodiments of FIGS. 32–35 enhance the gripping ability of the central portion on the tube because of the non-straight bands 26t. The tape of FIG. 34 may be used without a clip.

In FIG. 36 there is a showing of how the clamp 25 of FIGS. 7–9 may be used with any of the securing tape embodiments of the present invention. FIG. 36 shows this relative to tape 10 of FIG. 1 but it will be appreciated that the clip 25 may be applied in the same manner to the central portion of any securing tape embodiment. In this regard the clip 25 is clamped to the central portion 20 as shown to thereby securely hold the tube 24 relative to securing tape 10. The clamping should not be sufficiently tight to fully obstruct any flow through tube 24.

In FIGS. 37–40 yet another securing tape embodiment is shown. This embodiment includes a relatively wide end portion 12m and a relatively narrow end portion 12'm. The securing tape 12m has a nonadhesive outer surface and a pressure-sensitive adhesive 14m on its undersurface throughout its length which is covered by release paper 19m, which is removed for use. In use the right end of end portion 12m is adhesively secured to the skin 11, then a tube 24 is placed along the underside of area 60, and then narrow end 12'm is placed underneath the tube and through trapezoidal opening 61 and thereafter carried around over tape portion 60 and adhesively secured to the skin 11. By applying the tape in the foregoing manner, narrow end 12'm can be tightened around tube 24. While not shown, narrow end 12'm may be slitted in a manner such as shown in FIG. 2 to provide a plurality of longitudinally extending bands to enhance gripping of tube 24. Also, while not shown, the embodiment of FIGS. 37–40 can also be used with a clip.

Figure 41:
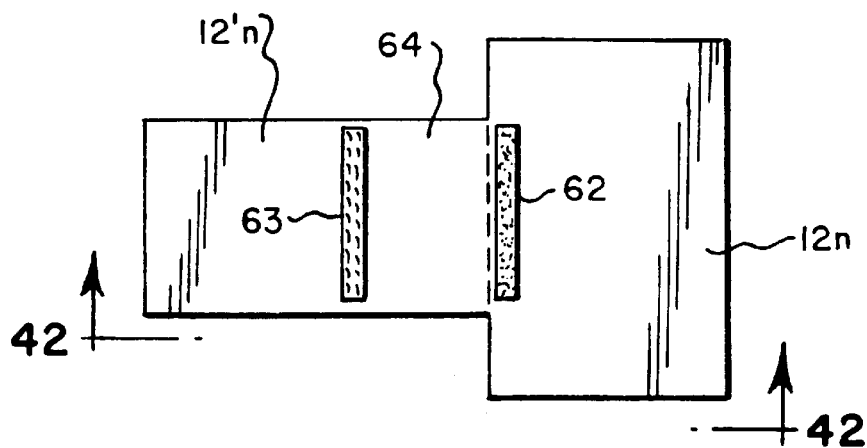
FIG. 41 is a plan view of yet another securing tape embodiment of the present invention which does not use a clip.
Figure 42:
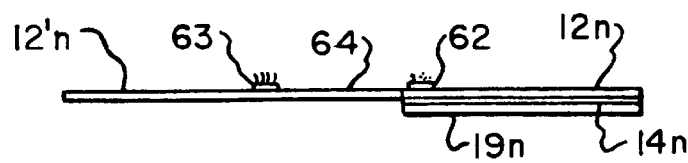
FIG. 42 is a side elevational view taken substantially in the direction of arrows 42—42 of FIG. 41.
Figure 43:
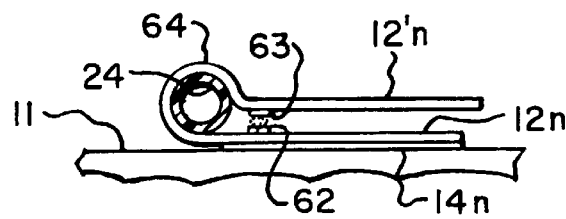
FIG. 43 is a side elevational view of the embodiment of FIG. 41 securing a tube to the skin of a patient.

In FIGS. 41–43 a further securing tape embodiment is shown having a nonadhesive upper surface. This embodiment includes a wide end portion 12n and a narrow end portion 12'n. The wide portion 12n has a layer 14n of pressure-sensitive adhesive thereon which is covered by release paper 19n. The narrow portion 12'n does not have adhesive on its under-surface. The securing tape has a strip of pile fastener material 62 adhesively attached to its upper surface as shown, and it has a strip of hook fastener material 63 adhesively attached to its upper surface as shown. In use a tube 24 is encircled by the portion 64 of narrow end 12'n between hook and pile fastener strips 62 and 63 after the wide portion 12n is adhesively secured to skin 11. Thereafter, the hook fastener 63 is secured to the pile fastener 62 to firmly secure the tube 24 as shown in FIG. 43. While not shown, the embodiment of FIGS. 41–43 may be used with a clip in the manner shown in FIG. 36.

Figure 44:
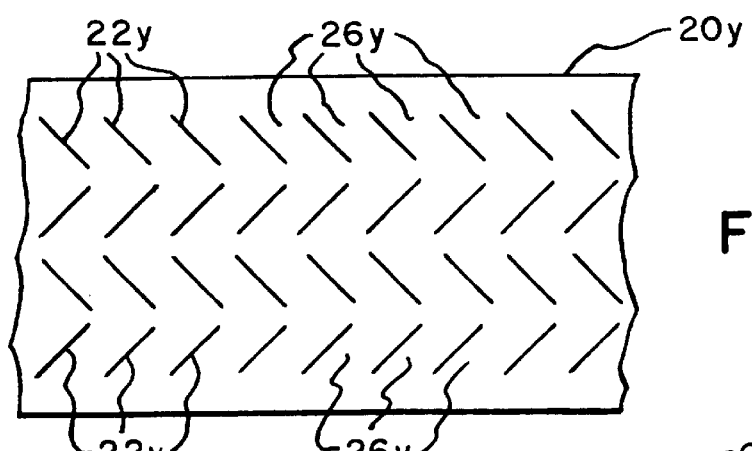
FIG. 44 is a fragmentary enlarged view showing a slit herringbone configuration which may be applied to various of the securing tapes rather than the longitudinal slits such as shown in the embodiment of FIG. 2.

In FIG. 44 a slit herringbone pattern is shown for use on the central portion 20x which represents the central portion of any securing tape disclosed in the present specification. The central portion 20y includes a plurality of slits 22y in a herringbone pattern, and this is intended to provide a series of adjacent bands 26y. This structure is an alternate to the longitudinal band structure, such as shown in FIG. 2, and it can be applied to any securing tape embodiment shown in the present specification except where inconsistent therewith.

Figure 45:
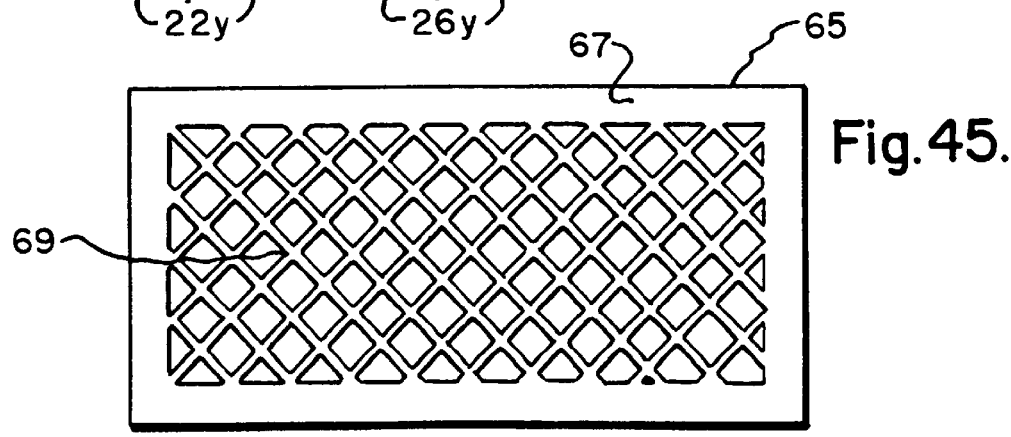
FIG. 45 is an enlarged plan view of a silicone grid which may be placed on the inside surface of a securing tape which encircles a tube.
Figure 66:
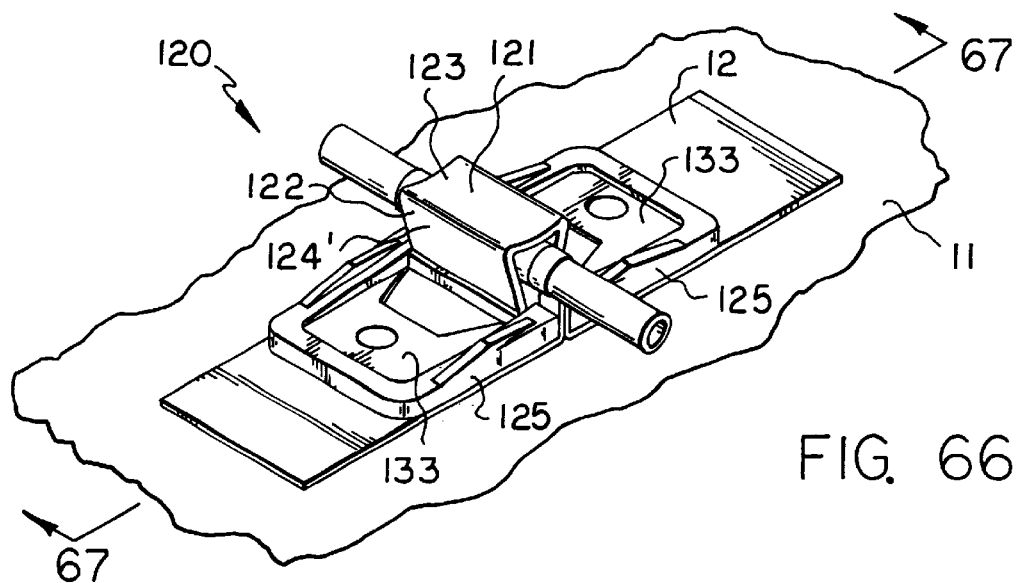
FIG. 66 is a fragmentary perspective view of another embodiment of a securing tape assembly mounted on the skin of a patient.
Figure 67:
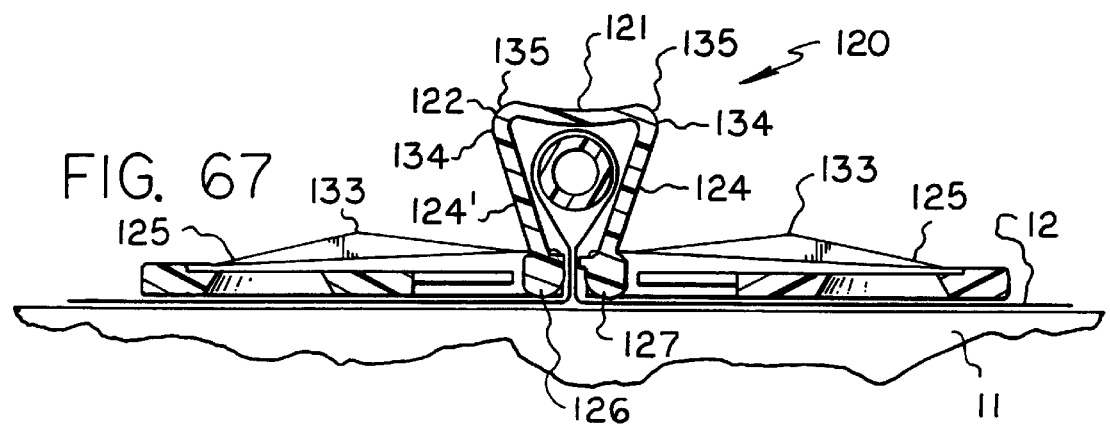
FIG. 67 is a cross sectional view taken substantially along line 67—67 of FIG. 66.
Figure 68:
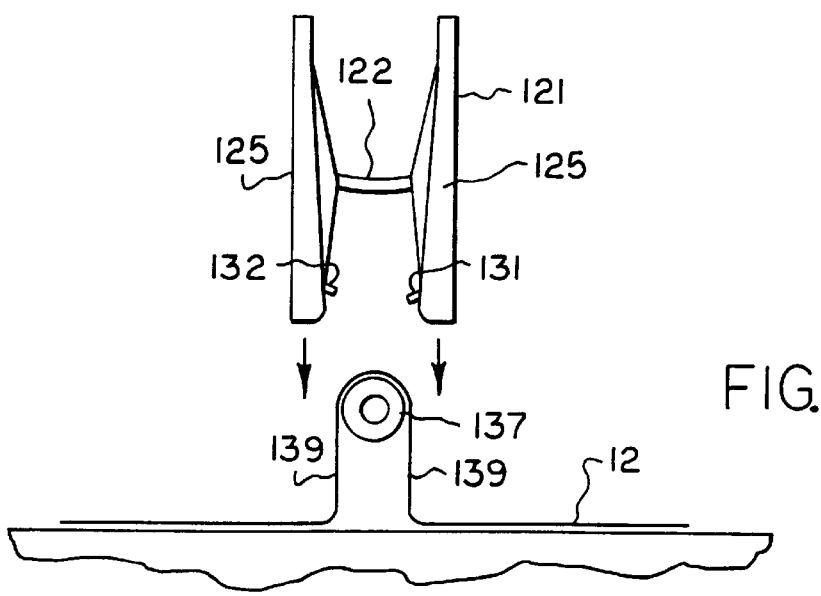
FIG. 68 is a side elevational view showing the securing tape portion mounted on the skin of a patient and showing the clip in an initial position during the process of being assembled with the securing tape portion.
Figure 69:
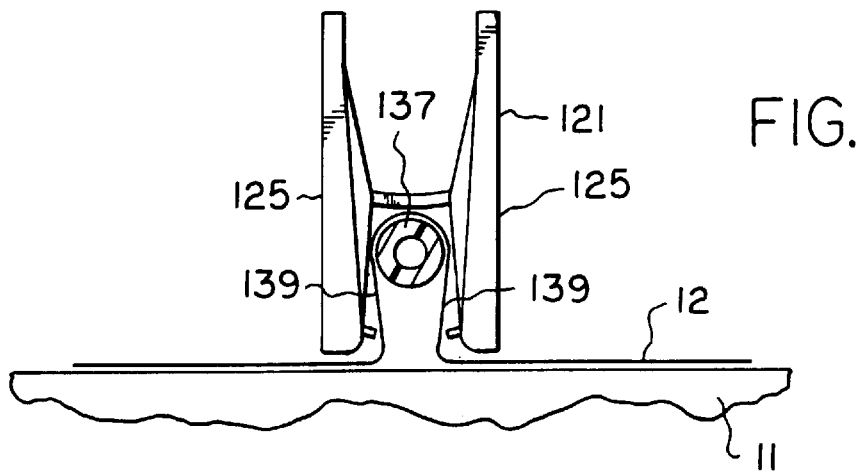
FIG. 69 is a view similar to FIG. 68 but showing the clip in more advanced position during the process of being assembled with the securing tape portion.
Figure 70:
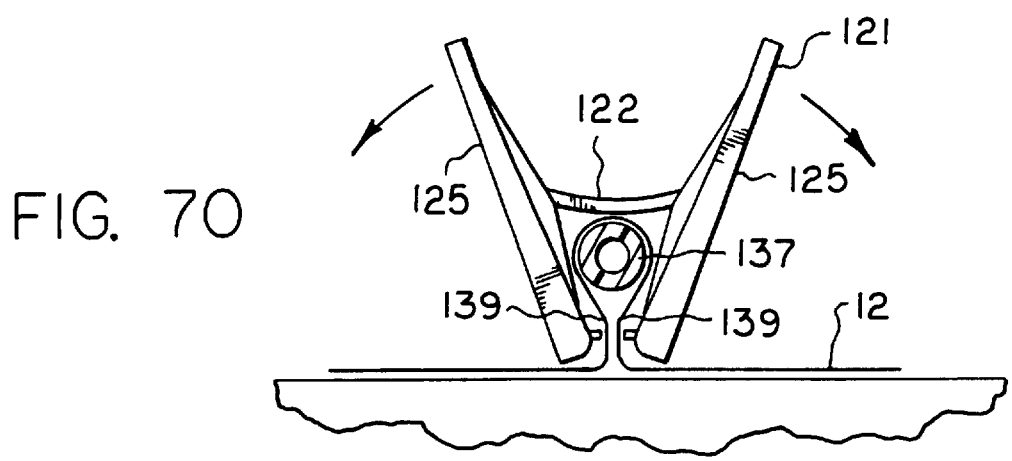
FIG. 70 is a view similar to FIG. 69 but showing the clip in a still further position during the process of being assembled with the securing tape portion.

In FIG. 45 a silicone grid pattern structure 65 is shown having a border 67 which encircles a grid 69. The silicone grid 65 is relatively thin on the order of about one millimeter. The grid 65 is of the size to be used underneath central portion, such as 20, of the embodiment of FIG. 2, or any other embodiment having a central portion of the shape such as central portion 20. The grid 65 is thus placed between the central portion of a securing tape and the tube so that it provides silicone rubber to silicone rubber contact with a silicone rubber tube such as 24. It has been found that there will be no slippage when there is contact of silicone rubber parts to each other.

In FIGS. 46–51 an improved clip embodiment 70 is shown for use as an alternate to the type of clip 25 shown in FIGS. 1, 7 and 8. Clip 70 is fabricated of suitable plastic, such as polyethylene, and it has two halves 71 and 71' which are connected by a living hinge 72. Fastening structures 73 are located at the ends of sides 71 and 71'. Projections 74 are located at the ends of side 71', and latches 75 are located at the ends of side 71. In use, sides 71 and 71' are spread apart about living hinge 72 and they are placed in encircling engagement with a tube 24 after a central portion 20 of a securing tape, such as 10 (FIG. 1), has been previously placed in encircling engagement about tube 24. The fastening structures 73 are positioned beyond the opposite edges of the central tape portion 20. Thereafter, the latches 75 at the ends of clip 70 are engaged over projections 74 to the positions shown in FIGS. 48 and 49 to clip the portions 79 and 79' of tape 10 therebetween. The internal diameter of clip halves 71 and 71' is preferably slightly less than the diameter of tube 24 to insure good gripping engagement between the securing tape central portion, such as 20, with tube 24. Thereafter, the ends, such as 17 (FIG. 1) of the securing tape are adhesively secured to the skin 11.

In FIGS. 52 and 53 a still further the embodiment of the present invention is disclosed. The securing tape may be identical in all respects to the tape embodiment of FIG. 12 except that the central portion 20' has a strip 80 of material thereon which is laminated to a thin sheet of foam 81. The material 80 is known as "blue abrasive" and it is identified as part number 45-012-00 of the Mercury Foam Company of Hackensack, N.J. In the embodiment of FIGS. 52 and 53, the numerals which are identical to the numerals of FIGS. 1–9 and 12 denote like elements of structure. In this respect the central portion 20' is unslitted, as is the embodiment of FIG. 12. In other words, the only difference between the embodiment of FIG. 12 and the embodiment of FIGS. 52 and 53 is that there is a strip of foam 81 adhesively secured to the center of central portion 20' and a strip of the blue abrasive material 80 is adhesively secured to foam 81. The embodiment of FIGS. 52 and 53 is used in the same manner as the embodiment of FIGS. 1–9, that is, with a clip 25 as shown in FIG. 1. Also, the clip can be of any suitable type.

In FIGS. 54 and 55 a still further tape embodiment of the present invention is disclosed. This embodiment is identical in all respects to the embodiment of FIG. 13 except that a strip 80 of blue abrasive material is adhesively secured to a strip of foam 81 which is adhesively secured to adhesive layer 14. In FIGS. 54 and 55 the adhesive layer 14 is exposed on opposite sides of the blue abrasive material 80. The embodiment of FIGS. 54 and 55 is utilized in the same manner as described above relative to FIG. 1, namely, with a suitable clip such as 25, or any other type of clip.

In FIG. 56 a still further embodiment of the present invention is disclosed. This embodiment is identical in all respects to the embodiment of FIG. 26 and like numerals denote like elements of structure. In this embodiment a strip 80 of blue abrasive material is adhesively secured to the underside of tab 41h with a layer 81 of foam therebetween. In use the embodiment of FIG. 56 functions in the same manner as that shown above in FIG. 22, namely, with a suitable clip.

In the embodiments of FIGS. 52–56, the blue abrasive strip material 80 frictionally grips the tube 24 (FIG. 1) so that it cannot move axially. The blue abrasive material also will not shed, and it is therefore manifestly suitable for use where a patient's skin is not intact.

In FIGS. 57–63 a still further securing tape embodiment is shown. To make the securing tape of FIGS. 61 and 62, a blank is utilized which is a tape 90 having a nonadhesive surface 91 and an adhesive surface 92 throughout its length which is covered originally by three sections of release paper 93, 94 and 95. The central release paper 94 is removed after a section of the tape and release paper is cut out to form a window or opening 96. The blank is folded up about its centerline 97 so that the adhesive surfaces 99 and 100 on the opposite sides of centerline 97 will adhere to each other. However, prior to this, a piece of hook fabric 101 is adhesively secured to nonadhesive surface 91 to one side of opening 96 and a piece of pile fabric 102 is adhesively secured to surface 91 on the opposite side of opening 96.

After the central portion of the tape containing adhesive surfaces 91 and 100 has been folded up, a tab 103 is formed as shown in FIGS. 61 and 62. Thereafter, a piece of polyurethane foam material 104 is adhesively secured to the portion of adhesive 99 which is exposed through opening 96.

The securing tape of FIGS. 57–62 is used in the following manner, as shown by the schematic representation of FIG. 63. The tab 103 is wound around a tube 105 so that the foam 104 firmly engages tube 105. Thereafter, the hook fabric 101 on the outer end of tab 103 is attached to the pile fabric 102 such that spaced portions 107 and 108 of tab 103 are spaced above the end portions 109 and 110 after the latter have been adhesively secured to the skin 111 of a patient. Thereafter, any one of the previously described clips, such as 25 (FIG. 7), is snapped around the spaced tab portions 107 and 108 to cause the foam 104 to firmly engage tube 105 against slippage.

The embodiment of FIGS. 57–63 is highly advantageous in that it is economical to make both from a material and a labor viewpoint and it provides an extremely reliable grip on a tube 104 against movement once it is secured within the tape by a clip.

In FIGS. 64 and 65 schematics are shown of a further modified embodiment of the present invention. The securing tape assembly 10r is a modification of the securing tapes of FIGS. 1–6 or it can be a modification of the securing tape of FIGS. 10 and 11. The securing tape of FIGS. 64 and 65 is used in the same manner as the securing tape of FIGS. 1–6 wherein portions 21 are placed in encircling engagement with a tube 24, or a needle may be substituted for the tube. A clip 25 is secured as shown and described above relative to FIGS. 1–7. The securing tape assembly 10r differs from the securing tape assembly 10 of FIGS. 1–6 in that the securing tape has hook fabric 115 attached to the portion 20 of the tape which encircles tube 24. Pile fabric 117 is secured to securing tape portion 17 which is adhesively secured to the skin 11 of a patient. It will be appreciated that the hook and pile fabrics can be reversed.

In use the central portion 20 is bent over so that the hook fabric 115 engages the pile fabric 117 to thereby hold the tube 24 or a needle securely against the skin 11 of a patient. It is to be noted that the numerals which appear in FIGS. 64 and 65 and which are identical to the numerals of FIGS. 1–6 denote like elements of structure. While the securing tape shown in FIGS. 64 and 65 has been described with respect to the securing tape of FIGS. 1–6, it will be appreciated that any of the securing tape embodiments discussed previously which are capable of being modified as discussed relative to FIGS. 64 and 65 can be used in the manner described above relative to FIGS. 64 and 65.

Figure 71:
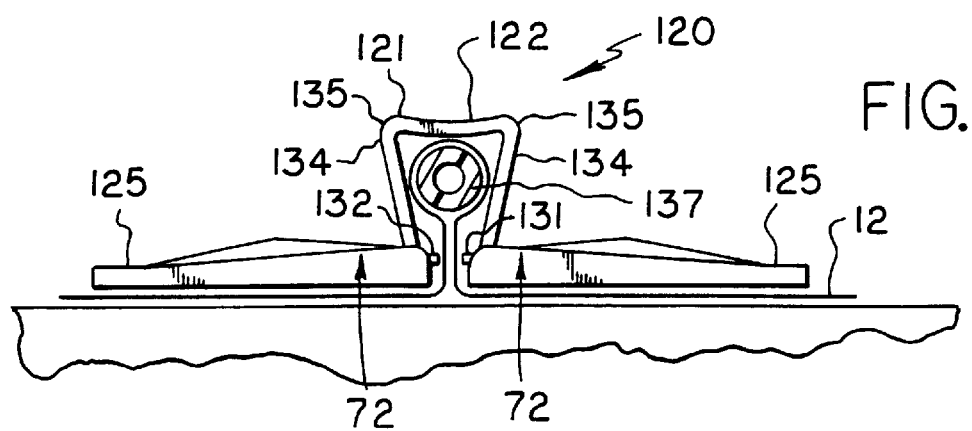
FIG. 71 is a view similar to FIG. 70 but showing the clip in its final clamped position relative to the securing tape portion.
Figure 72:
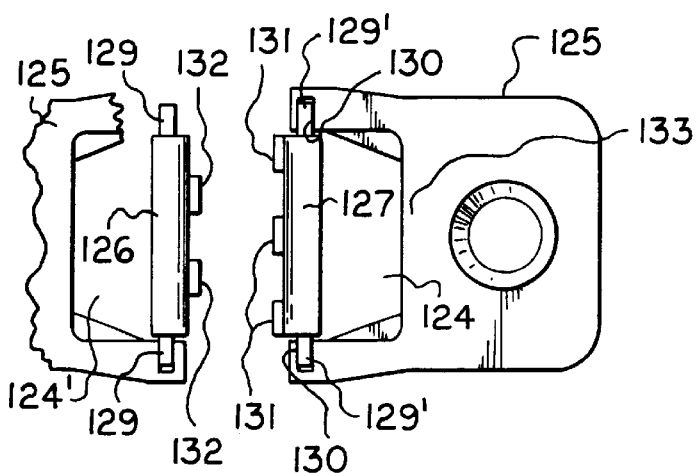
FIG. 72 is a view taken substantially in the direction of arrows 72—72 of FIG. 71 without the securing tape between the enlarged portions of the sides of the central portion of the clip.

In FIGS. 66–72 a securing tape assembly 120 is shown wherein a tape, such as 12 of FIG. 1, is shown attached to the skin 11 of a patient. Securing tape 12 is shown solely by way of example but it will be appreciated that the clip 121 of FIGS. 66–72 may be used with any of the preceding embodiments of securing tapes with which other types of clips have been used. Clip 121 is fabricated entirely of plastic and it is a commercial product having the trademark LAUREL and it is fabricated by Laurel Plastics of Aichwald, Germany. The clip 121 includes a central portion 122 of plastic which assumes the configuration shown in FIGS. 66, 67 and 71 when the clip is not stressed to an open position. Central portion 122 includes a top 123 and sides 124 and 124' which terminate at enlarged portions 126 and 127 (FIGS. 67 and 72) having pins 129 and 129', respectively, at their outer ends which are received in depressions 130 of tabs 125. As can be seen from FIG. 72, which depicts sides 124 and 124' spread apart for clarity, the right side 124 has teeth 131 and the left side 124' has teeth 132 which interfit with teeth 131 when central body portion 121 assumes its normal unstressed closed position. When the tabs 125 are pivoted to the position of FIGS. 68 and 69, the central portions 133 (FIG. 67) of tabs 125 will bear against the edge portions 134 of sides 124 to thereby cause sides 124 to pivot about hinge points 135 (FIG. 67) so that enlarged portions 126 and 127 will separate and teeth 131 and 132 will be spread apart. It is in this position of FIG. 68 that clip 121 can be moved in the direction of the arrows in FIG. 68 to move from the position of FIG. 68 to the position of FIG. 69 to thereby have tube 137 received between sides 124 with the portions of tape 12 being in position to be clamped as shown in FIG. 71 as the tabs 125 progressively move from FIG. 69 to FIG. 70 to FIG. 71. It is to be especially noted that once the teeth 131 and 132 have reached their final closed position, tabs 125 can be pivoted downwardly about pins 129 and 129' from the position of FIG. 70 to the position of FIG. 71 wherein they lie flush against the upper surface of securing tape 12.

Figure 73:
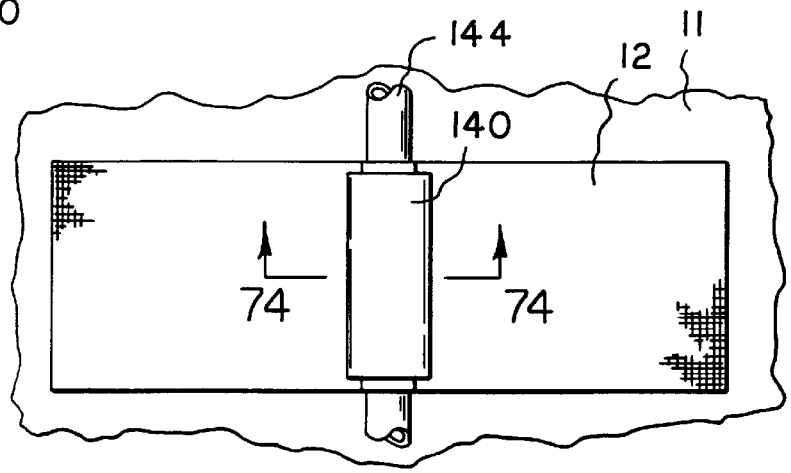
FIG. 73 is a plan view of another type of securing tape clip mounted on a securing tape mounted on the skin of a patient.
Figure 74:
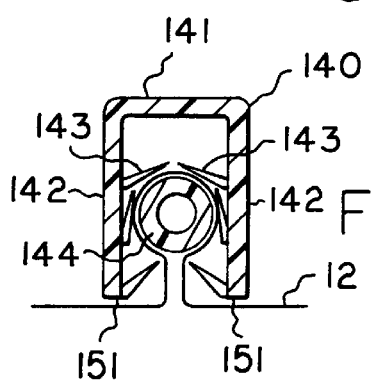
FIG. 74 is a fragmentary partially schematic cross sectional view taken substantially along line 74—74 of FIG. 73.
Figure 74A:
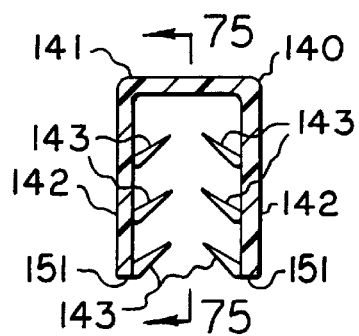
FIG. 74A is a cross sectional view of the clip of FIGS. 73 and 74 in a relaxed state.
Figure 75:
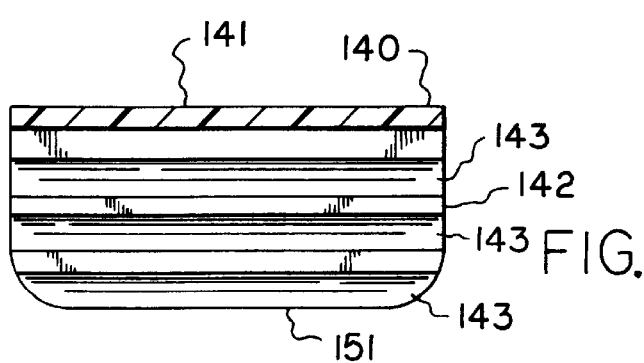
FIG. 75 is a cross sectional view taken substantially along line 75—75 of FIG. 74A.

In FIGS. 73–75 another securing tape clip 140 is shown wherein a tape, such as 12 of FIG. 1, is shown attached to the skin 11 of a patient. As noted above, securing tape 12 is shown solely by way of example, but it will be appreciated that the clip 140 of FIGS. 73–75 may be used with any of the preceding embodiments of securing tapes with which other types of clips have been used. Clip 140 is fabricated entirely of plastic and it comprises a very slightly flexible or rigid channel-shaped member having a top 141 and a pair of legs 142 with integral flexible fins 143 extending inwardly therefrom. The clip is applied in the manner shown in FIGS. 76 and 77. In this respect, after the tape 12 has been applied to the skin and around tube 144, the tube 144 is grasped between the thumb and forefinger proximate securing tape 12 and held downwardly against the skin of the patient. Thereafter, the end 145 of the clip 140 is held between the thumb and the forefinger of the other hand and pressed downwardly over the portion of the securing tape which overlies tube 144, the downward force being designated by arrow 147. After the lower corner of clip 140 in area 145 has firmly pressed the central portion of the tape against the tube and has possibly moved to a position where it is adjacent to the portion of the securing tape which is adhesively secured to the skin 11, pressure is applied in the direction of arrow 149 to the top of clip 40 at the end 150, while the tube 144 is held as shown in FIG. 77, until the lower edges 151 of clip 140 are sufficiently close to the portions of tape 12 which are adhesively secured to skin 11 so as to firmly hold the tape against the tube. When the clip 140 is fully installed, it will also assume the condition shown in FIG. 74 wherein the flexible fins 143 exert a pressure against the portion of the securing tape which encircles tube 144. When it is desired to remove clip 140 from its installed position of FIGS. 74 and 77, it is merely required to lift one of the ends of clip 140, for example, end 150 while holding the adjacent portion of tube 14 downwardly against the patient's skin 11 and thereafter remove the opposite end 145 from the securing tape while holding the adjacent portion of tube 144 downwardly against the patient's skin. It will be appreciated that a channel member without fins 143 can be used provided that its legs, such as 142, are sufficiently close to each other so as to firmly press the central portion of the tape against the tube.

In FIGS. 78–80 yet another securing clip embodiment 155 is shown. This clip may be similar to clip 140 in that it is a channel-shaped member made out of flexible plastic which has a top 157 and legs 159. Embedded in plastic channel is a metal channel 160 which extends throughout the length of clip 155. Molded integrally with legs 159 are flexible fins 161. The clip 155 is installed on a securing tape which holds a tube by merely moving it downwardly over the portion of the securing tape which is overlying the tube and thereafter pressing legs 159 inwardly as indicated by arrows 161 whereby the metal insert will cause the clip to retain a set such as shown in FIG. 80 wherein it clamps against the portion of the securing tape overlying the tube. The securing clip of FIGS. 78–80 is manufactured from elongated channels made by Outwater Plastics & Architectural Products, Inc. of Passaic, N.J. The clip 140 of FIGS. 73–77 is manufacturing from elongated plastic channels having the trademark SUPER GRIP U-CHANNEL and is identifiable as Part No. 811-5266-00 which is available from the manufacturer, Fasteners for Retail, Inc. of Cleveland, Ohio.

While preferred embodiments of the present invention have been disclosed, it will be appreciated that the present invention is not limited thereto but may be otherwise embodied within the scope of the following claims.

What is claimed is:

1. A securing tape assembly comprising an elongated tape having an inner surface and an outer surface, first means on said tape for securing said tape to a patient, second means on said tape for engaging a tube, and a clip for securing said second means to said tube with said second means being positioned between said clip and said tube.

2. A securing tape assembly as set forth in claim 1 wherein said second means comprise a central portion of said elongated tape.

3. A securing tape assembly as set forth in claim 2 wherein said central portion is positioned around said tube.

4. A securing tape assembly as set forth in claim 3 wherein said first means comprise end portions of said tape.

5. A securing tape assembly as set forth in claim 4 wherein said central portion is of less width than said at least one of said end portions.

6. A securing tape assembly as set forth in claim 2 wherein said second means includes foam material on said central portion.

7. A securing tape assembly as set forth in claim 2 wherein said clip is secured across said central portion of said tape.

8. A securing tape assembly as set forth in claim 2 wherein said clip is secured to end portions of said central portion.

9. A securing tape assembly as set forth in claim 1 wherein said second means comprises a tab.

10. A securing tape assembly as set forth in claim 9 wherein said tab is positioned substantially completely around said tube.

11. A tube and tape and clip combination comprising a tube, a tape, a portion on said tape for engaging said tube, and a clip securing said portion of said tape to said tube with said tape portion being positioned between said clip and said tube.

12. The combination as set forth in claim 11 wherein said tape includes end portions, and wherein said portion of said tape for engaging said tube comprises a central portion on said tape between said end portions.

13. The combination as set forth in claim 12 wherein said central portion is a tab.

14. The combination as set forth in claim 13 including pressure-sensitive adhesive on said end portions.

15. A securing tape assembly and tube combination comprising a tape having an inner surface and an outer surface, adhesive on said inner surface, a tube, a portion on said tape for engaging said tube, and a clip securing said portion of said tape to said tube with said tape portion being positioned between said clip and said tube.

* * * * *